United States Patent
Likuski et al.

(10) Patent No.: US 8,260,556 B2
(45) Date of Patent: Sep. 4, 2012

(54) CALIBRATION SURFACE METHOD FOR DETERMINATION ON OF ANALYTE RATIOS

(75) Inventors: Robert Likuski, Walnut Creek, CA (US); Roger Walker, Benicia, CA (US); Yabin Lu, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 792 days.

(21) Appl. No.: 12/196,132

(22) Filed: Aug. 21, 2008

(65) Prior Publication Data

US 2010/0049444 A1    Feb. 25, 2010

(51) Int. Cl.
    *G01N 33/50*      (2006.01)
    *G01N 33/481*      (2006.01)

(52) U.S. Cl. .......................... 702/19; 702/20

(58) Field of Classification Search .......................... None
See application file for complete search history.

(56) References Cited

U.S. PATENT DOCUMENTS

| | | | |
|---|---|---|---|
| 5,606,164 A | 2/1997 | Price et al. | |
| 6,210,971 B1 | 4/2001 | Messenger et al. | |
| 6,436,721 B1 * | 8/2002 | Kuo et al. | 436/514 |
| 6,898,451 B2 * | 5/2005 | Wuori | 600/322 |
| 2004/0019431 A1 | 1/2004 | Sterling et al. | |
| 2004/0023422 A1 * | 2/2004 | Miao et al. | 438/17 |
| 2005/0176089 A1 | 8/2005 | Ehrlich | |
| 2009/0024332 A1 | 1/2009 | Karlov et al. | |
| 2010/0049444 A1 | 2/2010 | Likuski et al. | |

OTHER PUBLICATIONS

Search/Examination Report dated Mar. 18, 2010 from International Patent Application No. PCT/US2009/053746, 12 pages.
International Application No. PCT/US2011/54136, International Search Report and Written Opinion mailed on Feb. 14, 2012, 13 Pages.
Hall, Jeffrey, W., et al., "Near-Infrared Spectrophotometry: A New Dimension in Clinical Chemistry," Clinical Chemistry, 1992, pp. 1623-1631, vol. 38, No. 9.

* cited by examiner

*Primary Examiner* — Jason Sims
(74) *Attorney, Agent, or Firm* — Kilpatrick Townsend & Stockton LLP

(57) ABSTRACT

The ratio of analytes is determined directly from the responses of the analytes using a conversion method. Individual analyte responses are obtained by using a selected measuring technique, and these individual responses are used as the independent variables in a conversion method. The dependent variable of conversion method is the desired analyte ratio. The resulting conversion method is then used to directly calculate the desired ratio of analytes as a function of the measured responses. No intermediate conversions, such as using a calibration curve to convert individual measured analyte responses to concentration values, are needed to obtain the desired ratio.

22 Claims, 24 Drawing Sheets

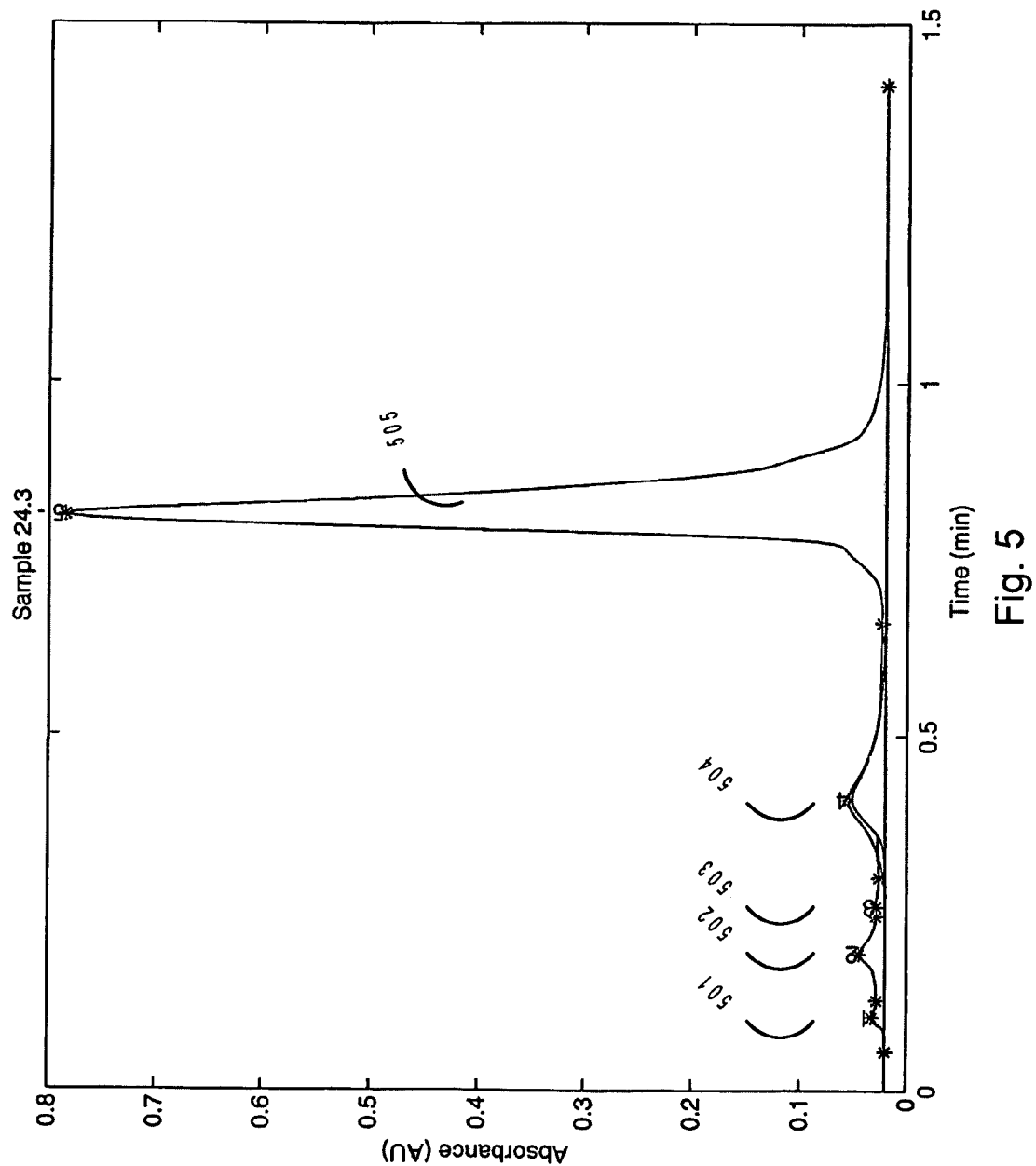

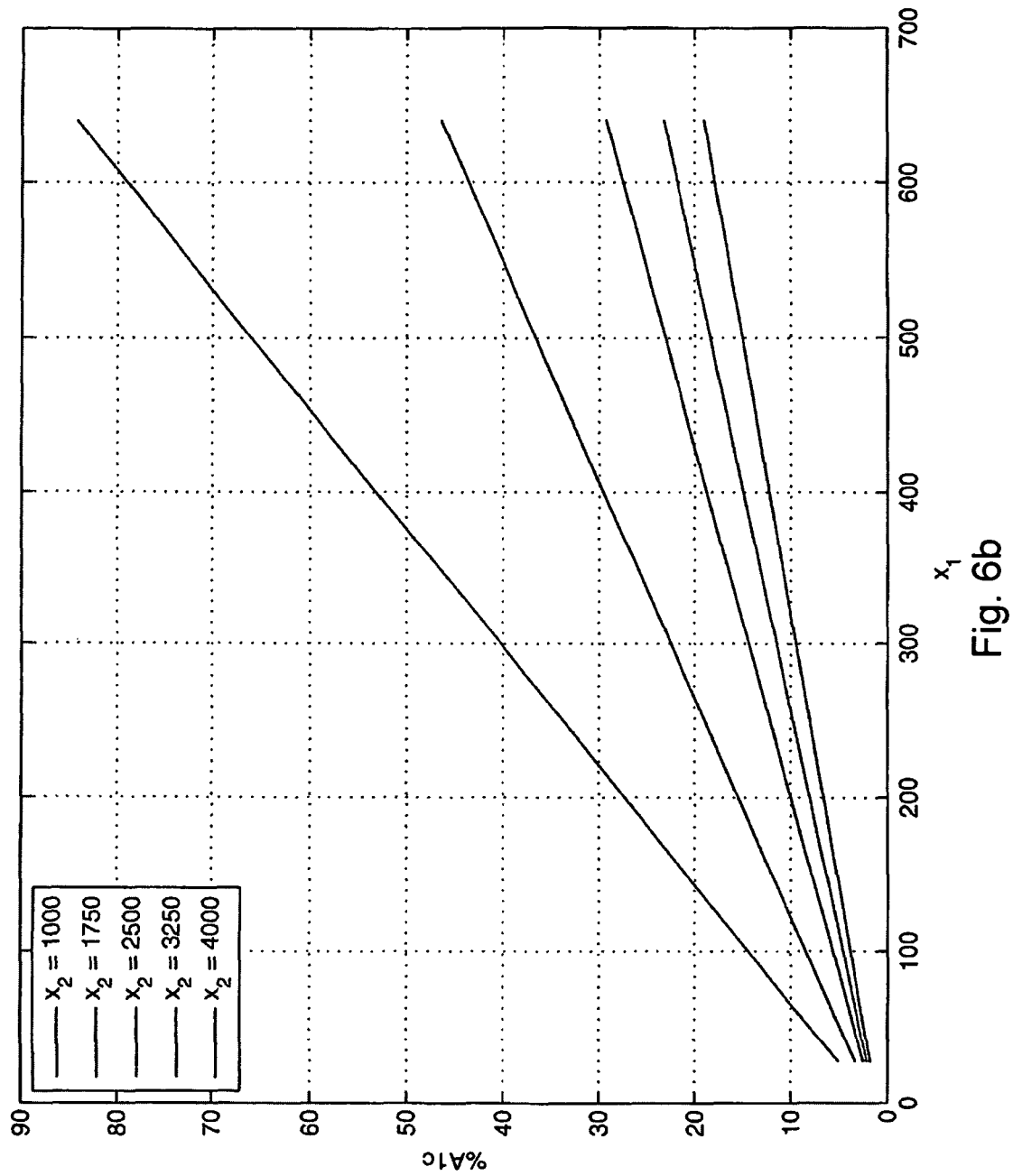

CALIBRATION SURFACE METHOD FOR DETERMINATION ON OF ANALYTE RATIOS

BACKGROUND OF THE INVENTION

1. Field of the Invention

The present invention relates generally to a method for measuring the ratio of analytes in a sample. The methods are generally applicable to any pair of analytes in which the result is expressed as a ratio. Additionally, multiple ratios can be expressed as ratios of multiple pairs of analytes

2. Description of the Prior Art

Computing the ratio of two or more analytes in a sample is a useful comparison in a variety of contexts. Ratios are frequently used to compensate for variability in the composition or concentration of the analytes in a sample. For example, when measuring analytes present in urine, the concentration of analytes in any given sample can vary significantly. These concentration fluctuations can be normalized by creating a ratio between different analytes present in a sample. For example, a ratio can be created between the concentration of a urinary analyte and the concentration of creatinine in urine. Creating this relationship between two analytes in the sample allows for a more meaningful measurement in light of the concentration fluctuations. It is also possible to normalize the concentration of a desired analyte in tissue against the concentration of total protein or a specific protein such as, for example, albumin. Ratios can also compensate for correlated errors in the measurement, e.g., dilution errors.

A brief description of the most common prior method for calculating the concentration ratio of analytes is illustrated in FIG. 1.

At step 101 a specimen is taken from a patient. Example specimens include blood, urine, or other bodily fluids. The specimen forms the basis for the sample from which a ratio of analytes will be measured and computed. The specimen does not necessarily have to come directly from a patient. The specimen may be available from another source.

At step 102, the specimen is converted into a pre-processed sample. A pre-processed sample can also be referred to as a test sample. This step may consist of anything done to the specimen before any analyte measurements are taken. For example, in certain embodiments, the specimen may be sampled and diluted by a specific amount. In other embodiments, an anti-coagulant may be added to the specimen. This step is optional as there may be times when the entire unaltered specimen will be used as the pre-processed sample.

The sample is measured in steps 103 and 104. In these two steps, the quantities of interest in the sample are presented as responses. Step 103 consists of all the processing done by the instrument to ready the pre-processed sample for reading. Processing the sample can involve a variety of steps. Using a multi-analyte sandwich immunoassay as an example, the sample is reacted with antibodies or specific binding reagents attached to a solid phase, the solid phase is washed to remove unbound material, reacted with one or more labeled antibodies or binding reagents, and washed to remove unbound labeled reagent for subsequent reading of the response. Other examples include high-performance liquid chromatography (HPLC), immunoassay, electrophoresis, capillary electrophoresis, ultra-violet/visible/infrared spectroscopy, raman spectroscopy, surface enhanced raman spectroscopy, mass spectroscopy, gas chromatography, or others. There may be instances when no processing steps need to be taken on the sample.

In Step 104, the selected reading technique is used to determine the response of each analyte in the sample that is to be used in the ratio. Step 104 is referred to as reading the analyte (responses). Reading techniques that may be appropriate include: fluorescence, absorbance, reflectance, ion current, electrochemical potential, optical density, color, surface plasmon resonance, or others. The processing and reading techniques chosen usually depends on the nature of the sample and analytes to be measured. The response of the analytes measured using the chosen measurement method can be in any unit that is appropriate for the selected method. These units could be fluorescence units, optical density, color, ion current, chemiluminescence units, electrical signal, or others. The analytes can also be measured in a multiplexed format, where many analytes are measured in a single pass, or they can measured in multiple, but separate individual assays.

The analyte responses are then converted into their corresponding concentrations. This step is shown at steps 105 and 106. Typically this conversion is accomplished using a device such as a calibration curve.

Each analyte response must be individually converted into a concentration value before a ratio of the analyte concentrations is calculated. A concentration value for an analyte can depend not only on the measured response of the given analyte, but also on the responses of other analytes in the sample because of cross-interactions such as cross-reactivity between analytes. The relationship between the response of an analyte in a sample measured using the selected measuring technique and the analyte's concentration in the same sample is typically nonlinear. Because of this non-linear relationship, the ratio of the analyte responses can be quite different than the ratio of the analyte concentrations. Therefore, it is necessary to compute the concentration of each analyte individually before computing the ratio if the ratio of the concentration of the analytes is to be computed.

A calibration curve is typically used to convert an analyte's response into a concentration value. A calibration curve for an analyte can be created by choosing a model for the curve and then determining the values of the model coefficients by measuring analyte responses from a set of samples where the concentration of the analyte is known before any measurement is taken. The analyte responses obtained from these known samples may be graphed to produce a calibration curve that is then used to infer what the concentration of an analyte is in a sample where the concentration is unknown. A separate calibration curve has to be created for each analyte response that is to be converted into a concentration value. In practice, the equation for the model with determined coefficient values may be used directly to determine the concentrations without graphing. Reference to a calibration curve is generally used because it is more illustrative than reference to a calibration equation.

At step 107 the individual concentrations calculated using the calibration curves are used to determine the desired analyte ratio. This can be done through a simple mathematical operation such as division. Ratios of analytes are typically unitless.

It is also sometimes necessary to adjust the ratio obtained in step 107 in order to make the measured ratio match what the ratio would have been using a different measuring technique. This step is shown at step 108. This extra conversion is done because it is often customary for a ratio to be presented as if the ratio was determined using a specific measuring technique, and this specific technique may not be the same technique used in steps 103 and 104. There may be well-known differences between the ratio of analytes obtained through these different measurement techniques, and the values can be converted between the two formats. Step 108 is an optional step depending on how the specific analyte ratio is to be ultimately presented. Additional information on standardized ratio measurements can be found in "Proposed changes for reporting HbA1c", IVD Technology (May 2007) and "Implementation of Standardization of Hemoglobin A1c Measurement", Clinical Chemistry, 54:6, 1098-1099 (2008). Both references are hereby incorporated in their entirety for all purposes.

This known method for determining the ratio of analytes has a number of problems. Interactions between the analytes in the sample can introduce inaccuracies in the known method. The response of one analyte can influence and change the response of the second analyte. For instance, in some measurement techniques, such as immunoassay, the first antibody used to measure the first analyte response may also interact with the second analyte in the sample. This cross-reaction would require a different calibration curve for the first analyte for each different value of the second analyte. A single average calibration curve could be created for the first analyte, but this would introduce inaccuracies in the responses obtained for that analyte. In addition, the second antibody could also react with the first analyte in the sample. This would compound the problem.

Another problem with the known method is that a calibration curve needs to be created and maintained for each analyte. This involves the choice of an appropriate calibration model and calibrators for each curve.

Another problem with the known method is that there is less opportunity to cancel noise that is correlated at the response level. The cancellation is done only during the determination of the ratio of the concentrations.

The proposed method for determining the ratio of analytes improves on the prior methods of determining the ratio of analytes by no longer directly using individual analyte concentrations as a part of the method. In addition to being more convenient to use, the proposed method produces more accurate analyte ratios because the proposed method inherently handles interferences introduced into the readings from interactions between analytes in a sample. It may offer additional advantages by requiring only a single calibration model and better cancellation of noise correlated at the response level.

BRIEF SUMMARY OF THE INVENTION

The proposed new method improves on the prior art by directly using the responses from a measuring method to obtain the ratio of analytes. No intermediate conversions, such as using a calibration curve to convert individual measured analyte responses to concentration values, are needed to obtain the desired ratio.

The ratio of analytes is determined directly from the responses using a single calibration surface rather than by taking the ratios of concentrations determined from the responses by using a pair of calibration curves. As with calibration curves, the calibration equation underlying the surface could be used without graphing the surface. As used here, the expression calibration surface is synonymous with the expression response surface. The calibration surface has the desired analyte ratio as the dependent y-axis and appropriate combinations of the responses as the independent $x_1$ and $x_2$-axes. The combination of the responses used for the $x_1$ and $x_2$-axes is chosen primarily to provide a simple model that fits the data. It can, however, also reduce the error in the final analyte ratio caused by correlated errors in the two analyte responses. A good fit reduces the lack-of-fit error and can reduce the number of calibrators needed to maintain the calibration surface. A good fit can also increase the time interval between calibrations. Different types of calibration may be done on different intervals. For example, lot specific calibrations may be done by the reagent manufacturer for a specific lot of reagents whereas laboratory calibrations may be done on a shorter interval by a laboratory running patient samples and controls.

The new method improves on the prior art in a number of ways. The new method no longer requires any intermediate conversions of analyte responses to analyte concentrations. Devices such as calibration curves are not necessarily specifically tailored to compute analyte ratios, and as a result the use of such devices as an intermediate step often plays a significant factor in many of the inaccuracies in the known prior methods.

The elimination of intermediate conversions also better handles any noise introduced into the measurement of the analytes. The responses of the analytes can be combined in a way to reduce noise common to the analyte responses. A combination of responses can be used to advantage as the independent variables in the regression model of the conversion method.

Additionally, any interactions between the analytes in a sample that can potentially interfere with measured analyte response are better accounted for in this method. This potential source of inaccuracy will also be present in the known samples used to create the regression model, and thus the inaccuracies will inherently be accounted for in the model. A pair of calibration curves, each tailored for a specific analyte, cannot handle these interferences and thus cannot handle this source of inaccuracy.

Another benefit of the proposed method is that if a linear (in the coefficients) regression model is used as is described below in some embodiments, then the regression model allows least-mean-square solutions of simultaneous equations rather than more general methods that minimize the least-mean-square error. This allows for faster and more robust calculation by avoiding the problem of finding a local rather than a global minimum associated with the more general methods.

Finally, the new method is more convenient than the prior method. After the regression model is created, no conversion to intermediate values through devices such as concentration vs. response calibration curves is required because the new method directly uses the responses obtained through the measuring process. Because there are fewer steps involved in the process once the regression model is created, it is more convenient for someone performing the new method to find the desired ratio.

One embodiment is directed to a method for determining one or more ratios of analytes in a sample. The method first measures the responses of two or more analytes in a sample using a selected measuring process to obtain two or more individual analyte responses. Next, one or more conversion methods are selected. These conversion methods define a ratio of analytes as a direct function of the individual analyte responses obtained using the selected measuring process. Finally, one or more ratio of analytes in the sample are computed using the selected one or more conversion methods and using the individual analyte responses obtained using the selected measuring process.

Another embodiment is directed to an apparatus for measuring the concentration ratio of two or more analytes. The apparatus comprises a measuring module capable of measuring the responses of analytes in a sample, a memory to store the measured analyte responses from the measuring module, a computer readable medium containing computer readable code having instructions for executing a conversion method that defines the analyte ratio of analytes as a direct function of the individual responses of the analytes obtained from the measuring module, and a processor to execute the computer readable code on the computer readable medium in order to calculate the concentration ratio of analytes using the conversion method.

Another embodiment is directed to a method for calculating a conversion method that defines the ratio of the analyte values of the analytes as a direct function of the individual responses of the analytes obtained from a measuring process. The method comprises selecting a statistically sufficient number of appropriate calibrators to be used to compute the conversion method, wherein said calibrators have a known ratio of the analytes, selecting a measuring process to be used to measure the responses of the analytes in the calibrators, measuring the responses of the analytes in the calibrators using the measuring process, selecting a regression model to be used to calculate the conversion method, and using the regression model to yield the conversion method wherein the regression model uses the responses of the analytes as the independent variables and the known analyte ratios as the dependent variable.

Another embodiment is directed to a computer-readable medium comprising code for measuring the responses of the analytes in a test sample using a selected measuring process, code for selecting a conversion method that defines the ratio of analytes as a direct function of the individual responses of the analytes obtained from the selected measuring process, and code for computing the ratio of the analytes of the test sample using the selected conversion method and the measured analyte responses from the test sample.

BRIEF DESCRIPTION OF THE DRAWINGS

FIG. 5 is a chromatogram produced by an HPLC measurement method.

FIG. 6b is a parametric representation of the Calibration Surface of FIG. 6a.

FIG. 8b is a parametric representation of the Calibration Surface of FIG. 8a.

FIG. 9b is a parametric representation of the Calibration Surface of FIG. 9a.

FIG. 10b is a parametric representation of the Calibration Surface of FIG. 10a.

FIG. 11b is a parametric representation of the Calibration Surface of FIG. 11a.

DETAILED DESCRIPTION OF THE INVENTION

Disclosed herein according to various embodiments are improved methods for calculating the ratio of analytes that can be implemented in a variety of embodiments tailored for a wide array of analytes. In particular, potential analytes for different embodiments can include proteins, peptides, carbohydrates, small molecules, nucleic acids, or any other material that can be measured and then expressed as a ratio.

General Description of Proposed Method

Figure 2:
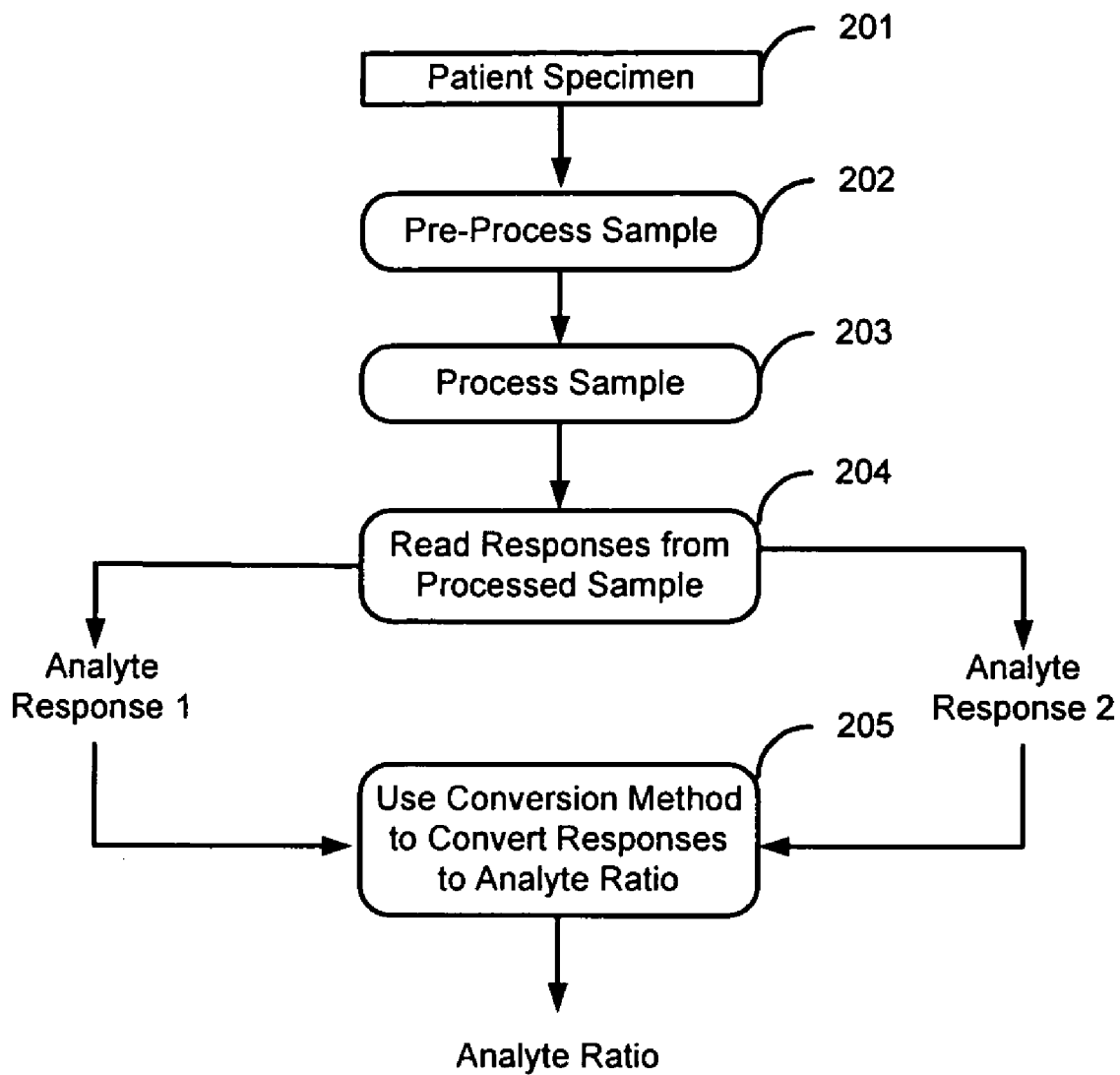
FIG. 2 is a flow chart depicting the proposed method for calculating the ratio of two generic analytes in a sample.

FIG. 2 illustrates the general steps involved in calculating the concentration ratio of two analytes according to one embodiment. As will be clear from this description, other embodiments of this proposed method can be easily altered to produce other types of analyte ratios by creating and using a different conversion method in the process.

Figure 1:
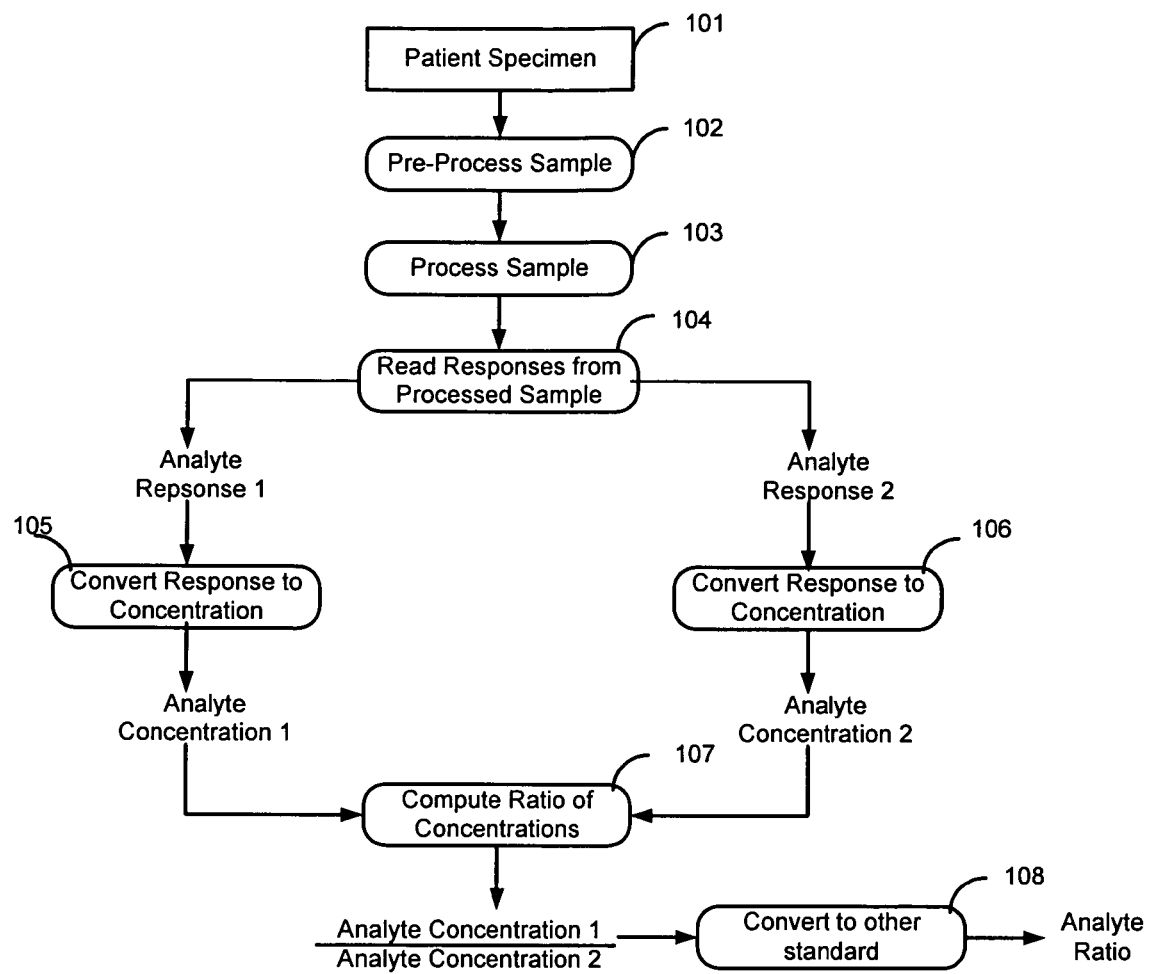
FIG. 1 is a flow chart depicting the known method for calculating the ratio of two generic analytes in a sample.

Steps 201-204 are essentially identical to steps 101-104 displayed in FIG. 1. At step 201, a patient specimen is obtained. At step 202, this patient specimen is converted into a pre-processed or test sample. Together, steps 203 and 204 comprise the measuring process. The sample is processed for reading at step 203 and read at step 204 producing a response for each analyte in the sample. As discussed in relation to the known methods, some of the above steps may be optional depending on the nature of the specimen and measuring technique used to measure analyte responses.

At steps 203 and 204 in FIG. 2, the selected measuring technique is used to measure the response of the analytes in the sample. The considerations for selecting a measuring technique in this step are similar to considerations at steps 103 and 104. The reading of the analyte responses in step 204 can be accomplished through a variety of techniques, such as by quantifying the fluorescence from fluorescent tags associated with either bound or unbound antibodies in the sample. The resulting responses from the selected measurement technique are listed as Analyte Response 1 and Analyte Response 2 in FIG. 2.

At step 205, the differences between the known methods for calculating the ratio of analytes and the proposed method become clear. In the embodiment shown in FIG. 2, this step uses a conversion method to directly convert the measured analyte responses to the desired analyte ratio. The conversion method is created before the process outlined in FIG. 2 began. The conversion method may be composed of a series of steps, as described further below. Multiple conversion methods can be used on the measured analyte response to obtain multiple analyte ratios. After the conversion is used to convert the analyte responses to the desired analyte ratio, the process is complete.

The conversion method in the embodiment of FIG. 2 can be any mathematical relationship that converts the analyte responses to the analyte ratio. In one embodiment of the proposed method, the conversion method consists of two steps. The first step combines or otherwise transforms the analyte responses to obtain two or more regression variables. The second step then uses the regression variables in a regression model to obtain the desired analyte ratio. The regression model may be a multiple linear regression model. The regression model may also use more complicated regression models.

The first step functionally combines the read analyte responses to obtain the two or more regression variables. For example, in one embodiment, a first regression variable may be set to be the ratio of two analyte responses and a second regression variable may be set to be one of the analyte responses standing on its own. Many other possible transformations are possible, and examples of other transformations are given in more detail later in this disclosure.

The second step of this embodiment of the conversion method uses a regression model to find the desired ratio as a function of the two regression variables. The dependent variable in the regression is the desired analyte ratio. This analyte ratio could be the concentration ratio or a ratio mathematically related to the concentration ratio, but it need not be. The transformation and regression model need to be created and the value of their coefficients determined before being used to determine the ratio of analytes in an unknown sample.

This transformation is used together with a regression model to determine the desired analyte ratio. It can incorporate step 108 of FIG. 1 and thus bypasses the need to calculate the ratio of concentrations as shown in FIG. 1. One purpose of the transformation is to reduce the number of regression terms needed to adequately fit the data. In some embodiments only a constant term, linear terms and possibly the product of the linear terms will be needed. In one embodiment, the combined transformation and regression coefficients are grouped into levels, defined by the time interval separating the determination of the coefficient values. For example, a three level grouping could consist of the following three levels: 1) Interval is determined by a user calibration schedule, 2) Interval is defined by the release of new reagent lots by the reagent manufacturer, 3) Interval is determined by a method or model change.

An outline of one embodiment of one method for jointly creating the transformation and regression model for an HbA1c embodiment is outlined below.

1. Generate a sample set covering the clinical range of HbA1c values and the range of total Hb concentrations to be accommodated by the method. The sample set is to be a grid of equally spaced values covering the range. Such a grid can be obtained by starting with a low and a high value and performing a set of dilutions. A 5×5 grid would be suitable if the transformation and regression model are not complex while a 9×9 grid would be suitable if they are complex. It may not be necessary to use a series of dilutions as outlined in this step if samples covering the desired concentration range are otherwise available.

2. Run the samples in triplicate. All of the responses will be used as both calibrators and unknowns in a process referred to here as auto-calibration.

3. Starting with a transformation and regression model containing the least number of terms that could be expected to meet the Lack-of-Fit acceptance criteria, optimize the transformation coefficients and determine the value of the regression model coefficients.

4. Systematically add terms to either the transformation or the regression model until the Lack-of-Fit acceptance criteria are met.

More specifics on this HbA1c embodiment are contained later in this disclosure.

Figure 3:
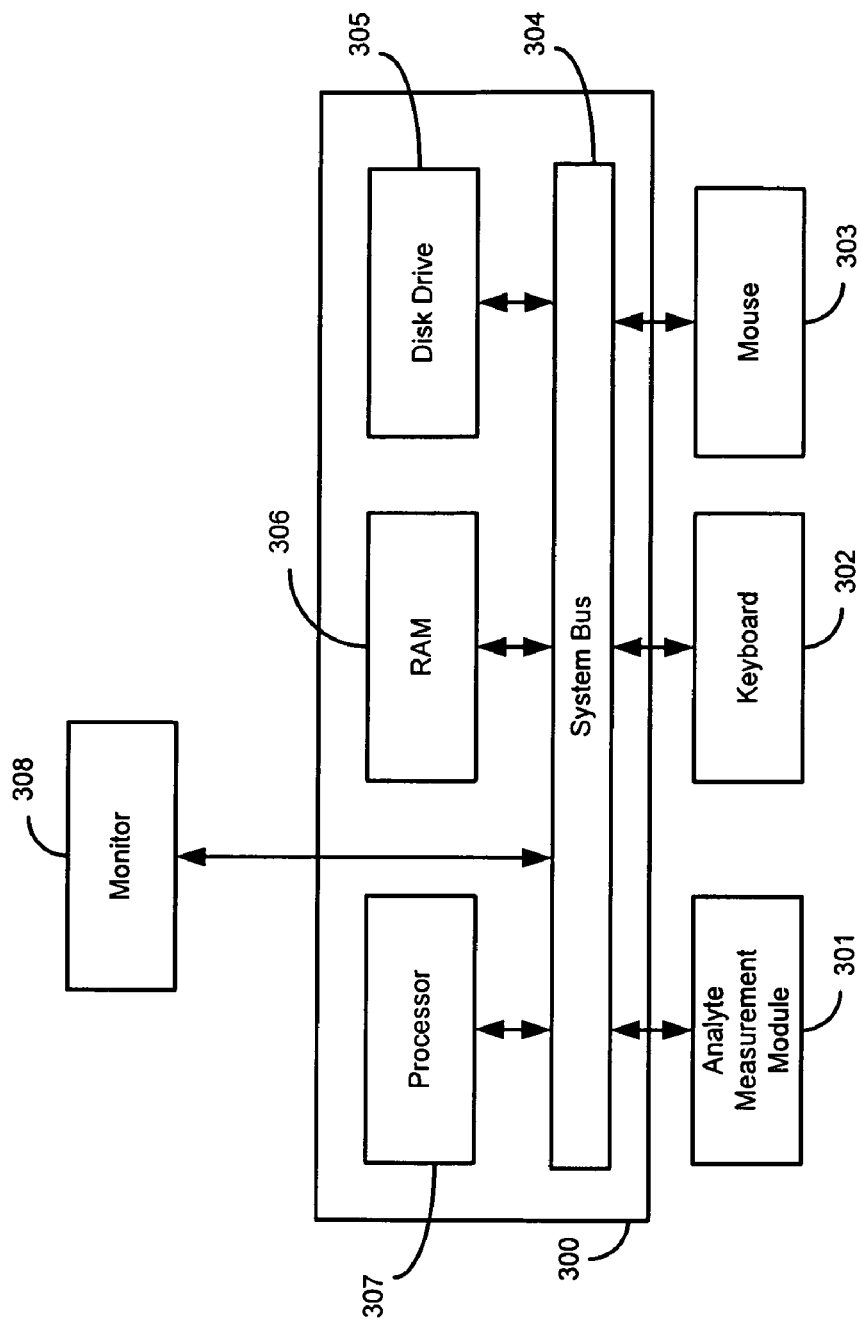
FIG. 3 is a block diagram of a computer system that can be used to execute the present invention.

FIG. 3 is a block diagram of a computer system 300 that can be used to execute one embodiment of the invention. The computer system 300 has a number of input modules. An Analyte Measurement Module 301 is used to measure the analyte responses in a test sample. This module will vary between different embodiments of the invention depending on the measurement method selected to measure the analyte responses. Also shown are a standard keyboard 302 and mouse 303. The computer system 300 also contains a variety of typical computer components inside the computer. These components include a system bus 304, one or more disk drives 305, RAM 306, and a processor 307. Other components can also be present depending on the exact nature of the embodiment. FIG. 3 also shows a monitor 308 that allows information to be displayed to a user of the system.

In one embodiment of the invention, the pre-processed sample that was created as in step 202 is placed in the Analyte Measurement Module 301 where the sample is further processed and the analyte responses in the sample are measured. This information is then transferred into the computer system along a system bus 304, and an appropriate conversion method is applied to the analyte response data using the processor 307. The instructions the processor 307 executes to implement the conversion method are stored on a computer readable medium such as the RAM 306 or disk drive 305. The conversion method can also be stored on this same media. The resulting ratio can then be displayed on the monitor 308. Alternative embodiments of the invention can output the analyte ratio using other communications means. For example, the computer system could print the measured ratio using a printer or send the measured ratio to another computer over a network.

Hemoglobin Embodiment

One embodiment of the proposed methods is focused on the measurement of HbA1c. HbA1c is one specific type of glycosylated hemoglobin that is the most commonly measured in diabetics. The human red blood cell allows glucose to freely pass into it, and glycosylated hemoglobin HbA1c refers to the hemoglobin components that has formed via the attachment of glucose sugars to the N-terminal valine of the beta chain of the hemoglobin molecule. In non-diabetics, over 90% of total hemoglobin is non-glycosylated. HbA1c itself will typically constitute about 4-7% of total hemoglobin. In diabetics, the percentage concentration of HbA1c can be in excess of 20% of total hemoglobin in patients that have poorly controlled their blood glucose levels.

Glycosylated hemoglobin is formed at a rate that is directly proportional to the ambient glucose concentration in the blood. The reaction between glucose and hemoglobin is ultimately irreversible and slow. The result is that only a fraction of total hemoglobin is glycated during the 120 day lifespan of a human red blood cell. As a result of this, the concentration of glycosylated hemoglobin in the blood provides a weighted moving average of blood glucose levels that can be used to monitor long-term blood glucose levels. This moving average, covering a 2-3 month time period, allows for an assessment of glycemic control in a diabetic patient. The ratio of the concentration of HbA1c to total hemoglobin has become a common method for measuring the health status for patients with diabetes.

HbA1c levels can be expressed in many ways, and one accepted way for doing so is to express HbA1c in National Glycohemoglobin Standardization Program (NGSP) units as a percentage of total hemoglobin (% HbA1c). Another accepted way is to express HbA1c in International Federation of Clinical Chemists (IFCC) units of mmole HbA1c/mol total Hb. In addition to the factor of 10 difference in units, there is also a difference because of the different reference methods used in the two standards. Other hemoglobin variant proteins, such as HbS, HbC, HbE, HbA2, and HbF can also be expressed as a percentage of total hemoglobin.

HPLC Method for Measuring HbA1c

One embodiment of the proposed method uses an HPLC technique for measuring HbA1c.

Figure 4:
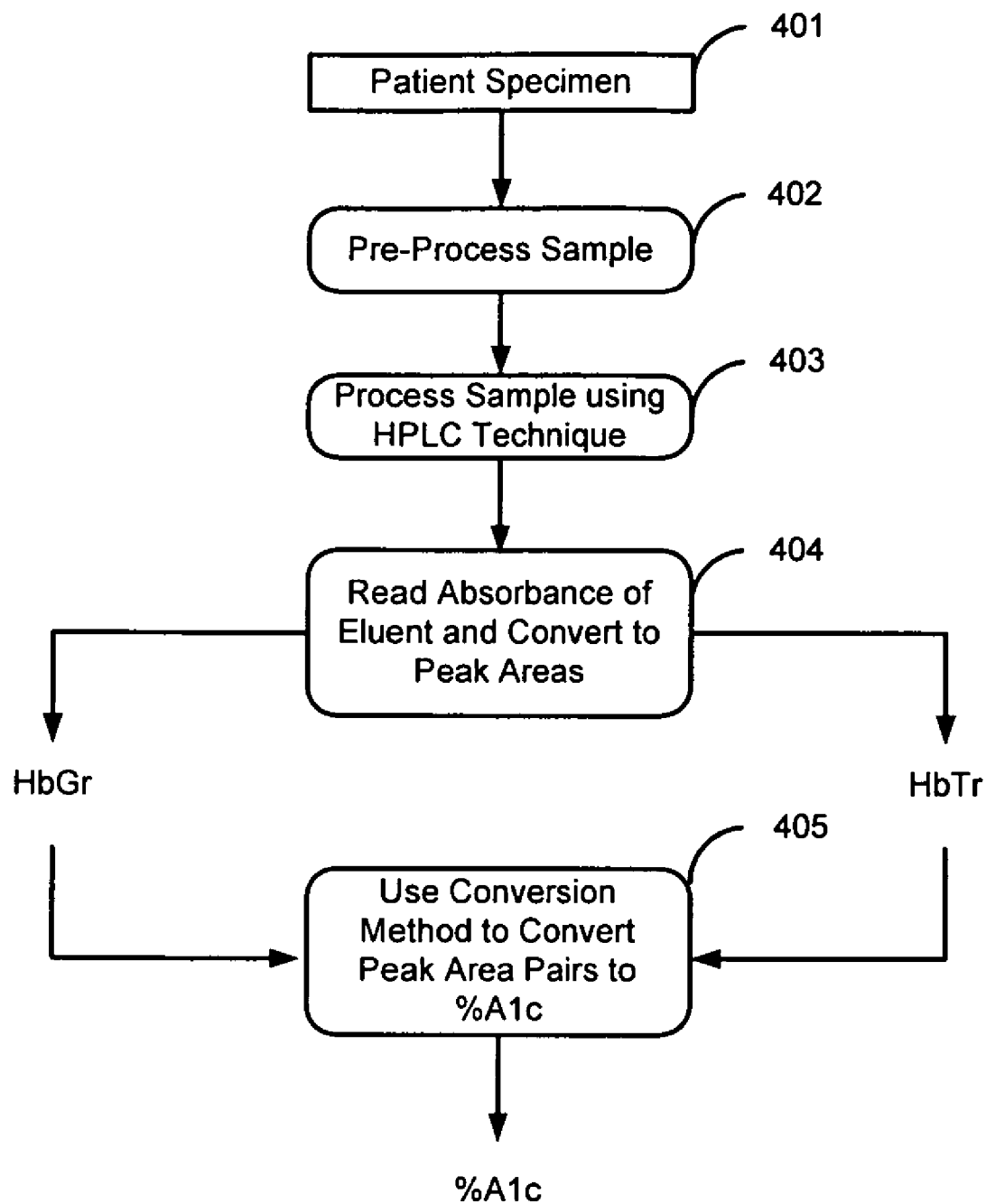
FIG. 4 is a flow chart depicting the proposed method for calculating % A1c through a HPLC measurement method.

FIG. 4 illustrates the steps involved in calculating the ratio of HbA1c to total hemoglobin according to an HPLC method of measuring HbA1c according to one embodiment.

Steps 401-404 are essentially identical to steps 101-104 displayed in FIG. 1 and steps 201-204 in FIG. 2. At step 401, a patient specimen is obtained. At step 402, this patient specimen is converted into a pre-processed sample, and at step 403, HPLC is used to separate this pre-processed sample into its component parts which elute from the chromatography column as a time series of peaks. At step 404 the components pass sequentially through the flow cell of an absorbance detector which converts the concentrations of the eluents to absorbance values that can be visualized as a chromatogram. The peaks in the chromatogram correspond to distinct components in the pre-processed sample. The areas of the peaks are then determined. The response for the glycosylated component of hemoglobin, HbGr, is determined as the area of a single peak while the response for the total component, HbTr, is the sum of the areas of selected peaks.

Table 1 is a tabulation of the response data from a prepared 5×5×3 sample set. The first two columns contain the HbGr and HbTr responses in mAU-sec and the third column uses a combination of three digits to identify the sample according to its place in the 5×5×3 sample grid. The first digit of the ID corresponds to the % A1c level, the second digit of the ID corresponds to the HbTc (Total hemoglobin concentration) level, and the third digit of the ID is the replicate number. Levels 11 corresponds to % A1c=5.365% and HbTc=0.42 gm/L. Levels 55 correspond to % A1c=17.420% and HbTc=2.1 gm/L. The remaining levels are equally spaced in value between levels 11 and 55. For this sample set, dilution is done during the pre-processing step rather than the processing step.

TABLE 1

| HbGr mAU-sec | HbTr mAU-sec | ID |
|---|---|---|
| 27.874 | 825.532 | 11.1 |
| 28.142 | 835.368 | 11.2 |

TABLE 1-continued

| HbGr mAU-sec | HbTr mAU-sec | ID |
|---|---|---|
| 27.789 | 828.799 | 11.3 |
| 57.043 | 1641.812 | 12.1 |
| 56.932 | 1643.280 | 12.2 |
| 55.839 | 1638.694 | 12.3 |
| 86.996 | 2467.903 | 13.1 |
| 87.044 | 2459.777 | 13.2 |
| 86.062 | 2445.601 | 13.3 |
| 117.456 | 3256.589 | 14.1 |
| 119.026 | 3261.055 | 14.2 |
| 118.241 | 3258.822 | 14.3 |
| 153.309 | 4102.811 | 15.1 |
| 156.254 | 4108.235 | 15.2 |
| 153.971 | 4087.014 | 15.3 |
| 46.377 | 831.970 | 21.1 |
| 46.392 | 833.943 | 21.2 |
| 46.363 | 829.997 | 21.3 |
| 96.064 | 1647.040 | 22.1 |
| 95.818 | 1644.891 | 22.2 |
| 95.366 | 1635.990 | 22.3 |
| 150.889 | 2500.300 | 23.1 |
| 150.066 | 2471.254 | 23.2 |
| 151.467 | 2469.004 | 23.3 |
| 208.266 | 3248.588 | 24.1 |
| 210.694 | 3245.441 | 24.2 |
| 210.551 | 3245.939 | 24.3 |
| 275.539 | 4055.995 | 25.1 |
| 280.168 | 4056.226 | 25.2 |
| 280.449 | 4063.696 | 25.3 |
| 65.376 | 835.830 | 31.1 |
| 64.936 | 835.760 | 31.2 |
| 65.002 | 832.391 | 31.3 |
| 136.513 | 1652.592 | 32.1 |
| 137.408 | 1660.416 | 32.2 |
| 137.788 | 1654.845 | 32.3 |
| 216.058 | 2487.202 | 33.1 |
| 218.470 | 2491.033 | 33.2 |
| 217.267 | 2484.372 | 33.3 |
| 303.501 | 3297.756 | 34.1 |
| 307.621 | 3297.322 | 34.2 |
| 309.769 | 3299.064 | 34.3 |
| 406.586 | 4149.740 | 35.1 |
| 403.200 | 4117.404 | 35.2 |
| 405.964 | 4084.984 | 35.3 |
| 82.488 | 830.766 | 41.1 |
| 82.900 | 829.330 | 41.2 |
| 83.236 | 827.317 | 41.3 |
| 175.422 | 1636.971 | 42.1 |
| 175.380 | 1632.871 | 42.2 |
| 176.416 | 1632.987 | 42.3 |
| 285.797 | 2496.466 | 43.1 |
| 285.513 | 2491.663 | 43.2 |
| 287.114 | 2490.088 | 43.3 |
| 396.906 | 3294.759 | 44.1 |
| 399.981 | 3304.702 | 44.2 |
| 399.531 | 3299.483 | 44.3 |
| 519.127 | 4145.395 | 45.1 |
| 521.490 | 4140.787 | 45.2 |
| 524.599 | 4149.083 | 45.3 |
| 103.458 | 841.094 | 51.1 |
| 103.671 | 841.246 | 51.2 |
| 103.402 | 836.941 | 51.3 |
| 198.905 | 1518.826 | 52.1 |
| 199.666 | 1513.088 | 52.2 |
| 201.716 | 1519.143 | 52.3 |
| 323.081 | 2311.261 | 53.1 |
| 324.312 | 2307.017 | 53.2 |
| 326.948 | 2310.868 | 53.3 |
| 475.945 | 3247.011 | 54.1 |
| 477.792 | 3243.755 | 54.2 |
| 479.228 | 3245.260 | 54.3 |
| 636.777 | 4201.339 | 55.1 |
| 640.934 | 4190.424 | 55.2 |
| 638.855 | 4195.881 | 55.3 |

FIG. 5 is a chromatogram illustrating this separation. It corresponds to the sample labeled in the third column of Table 1 as ID=24.3. The HbGr value in Column 1 corresponds to the area of the peak labeled 504, expressed in units of mAU-sec. That peak is the second and larger of two overlapping peaks identified by a single peak crest. The smaller peak in the pair is too small to be identified. The HbTr value in Column 2 corresponds to the sum of the areas of the peaks labeled 501, 502, 504 and 505, also expressed in units of mAU-sec. These are all A (Adult) components of hemoglobin. Peak 503 is identified as an F (Fetal) component and thus not included in the sum.

Four variations representing four different embodiments are described below. Each variation is defined by a model and a transformation. Each variation is constructed using the HPLC data in Table 1 in its model and transformation. The equation for the Model has the form:

$$y = \beta_{00} + \beta_{10}x_1 + \beta_{01}x_2 + \beta_{11}x_1x_2 + \ldots + \beta_{mn}x_1^m x_2^n$$

in which $x_1$ and $x_2$ are transformed variables defined in terms of the analyte responses. This equation represents a polynomial regression in which the variables are products of the analyte responses raised to integer powers HbGr (represented by $z_1$) and HbTr (represented by $z_2$) are transformed using the Transforms:

$$x_1 = \lfloor (z_1 - a_{12})^{a_{11}} - a_{13} \rfloor \div \lfloor (z_2 - a_{22})^{a_{21}} - a_{23} \rfloor$$

$$x_2 = \lfloor (z_2 - b_{12})^{b_{11}} - b_{13} \rfloor \div \lfloor (z_1 - b_{22})^{b_{21}} - b_{23} \rfloor$$

These equations define the calibration surface. The coefficients for these equations are determined using samples where the values of y are known. The responses $z_1$ and $z_2$ are determined by measurement. Once the coefficients are determined, measured responses can then be used to determine the value of y for an unknown sample. For the measurement of HbA1c in a hemoglobin method, y corresponds to % HbA1c, commonly referred to as % A1c.

The calculations used to illustrate these variations are done using scripts developed in MATLAB (© The MathWorks, Inc.). Other applications could also be used for this modeling. The particular Model and Transformations used in these variations will thus be expressed in a notation based on a MATLAB format for representing matrices. For the Model, the terms included are designated by a pair of integers corresponding to the subscripts in the equation for the Model. Members of the pair are separated by commas. Different pairs are separated by a semicolon. Square brackets are used to identify the set of pairs. For the transformations, standard MATLAB matrix notation is used with the first transformation designated by the matrix A and the second by the matrix B.

For example, A=[5, 5, 1; 1, −5, 3] would correspond to $a_{11}=5$, $a_{12}=5$, $a_{13}=1$, $a_{21}=1$, $a_{22}=-5$, and $a_{23}=3$. The Model term corresponds to the power of $x_1$ or $x_2$ for a given term in the model. For example, Model=[0,0; 1,0; 0,1; 1,1; 1,2; 1,3] corresponds to the model: $y = \beta_{00} + \beta_{10}x_1 + \beta_{01}x_2 + \beta_{11}x_1x_2 + \beta_{12}x_1x_2^2 + \beta_{13}x_1x_2^3$. The B terms work in a similar manner.

In determining the values of the Model Coefficients, the transformed data is scaled to prevent round-off error. The scaled coefficient values are presented in the same order as they appear in the Model. Scaling is done by dividing the HbGr data by Scale A and the HbTr data by Scale B. The scaling values are presented together with the coefficient values.

In all variations, a process referred to as auto-calibration is used. All of the 75 samples in the data matrix are used as calibrators and then as unknowns. The errors thus determined are within run errors. Using a standard technique referred to as "Analysis of the Components of Variance" these within run errors are expressed as variance and divided into components. Two components of interest are replicate error (also referred to as pure error) and lack-of-fit (LOF) errors. The replicate error is an indicator of the quality of the data and the lack-of fit error an indicator of the quality of the transformations and model used to transform the data and model the transformed data. There are two components of the lack-of-fit error. The higher level component is associated with how well the model accommodates different values of % A1c and the lower level with how well it accommodates different values of total hemoglobin concentration, HbTc, for distinct values of % A1c.

Variation 1: Linear in $x_1$ With No Transformation of Variables

A=[1, 0, 0; 0, 0, 0] B=[1, 0, 0; 0, 0, 0]
Model=[0,0; 1,0; 0,1; 1,1; 1,2; 1,3]
Coefficients=[1.6899; 84.6864; −0.4049; −154.6571; 110.0661; −27.0000]
for Scale A=300 and Scale B=2500.

Figure 6A:
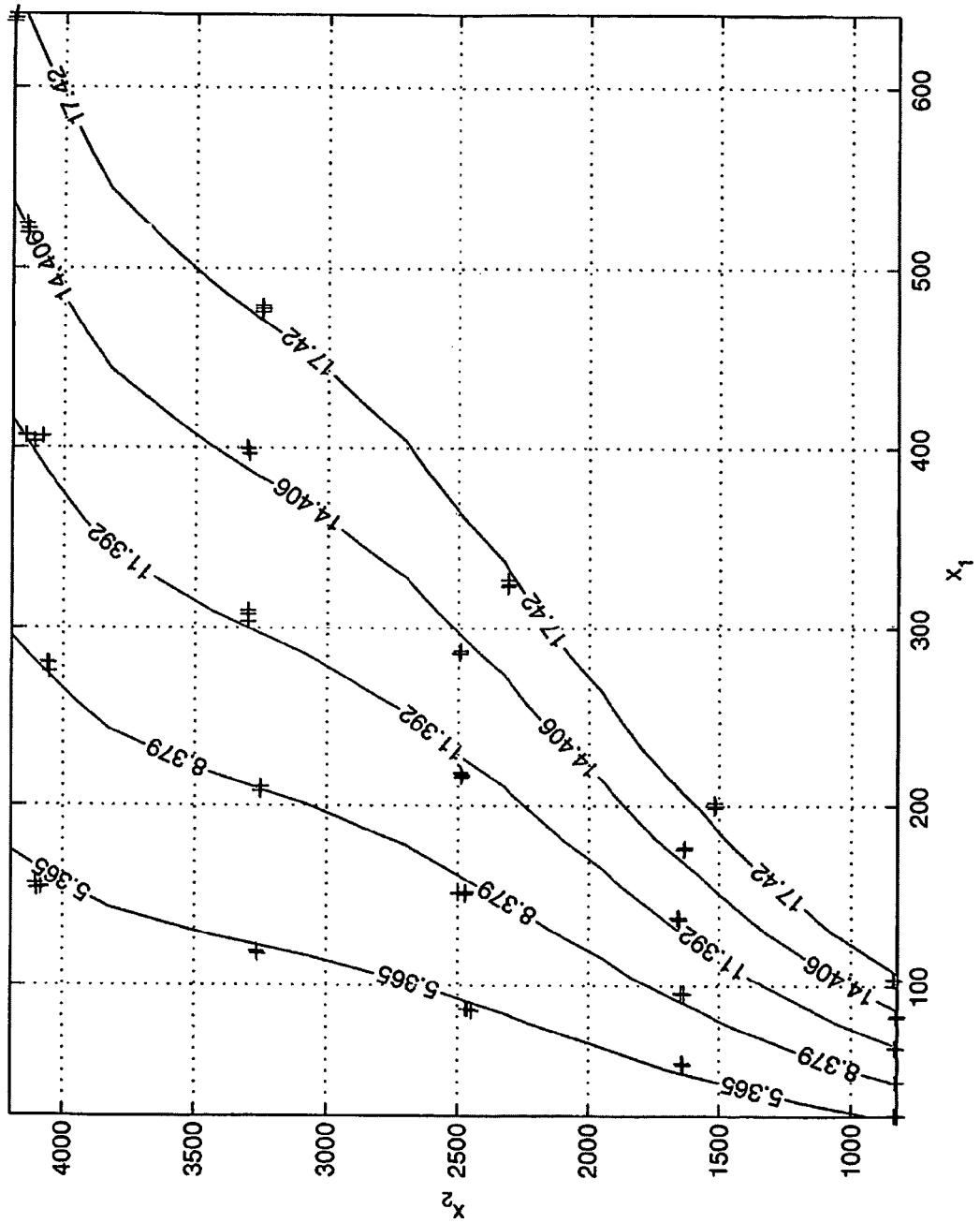
FIG. 6a is a contour plot giving a representation of the calibration surface for Variation 1 of the application of the Calibration Surface method to responses obtained by HPLC.

FIG. 6a is a contour plot of the resulting calibration surface. The contours on the contour plot represent the constant values of % A1c shown with the contour label. The "+" symbols are the data values of $x_1$ and $x_2$.

FIG. 6b is a parametric plot of the resulting calibration surface. The different lines in the parametric plot correspond to constant values of $x_2$, corresponding to equally spaced horizontal lines in the contour plot. The legend with the plot shows these $x_2$-values. From top to bottom, the legend values are in the same order as the lines.

Figure 6C:
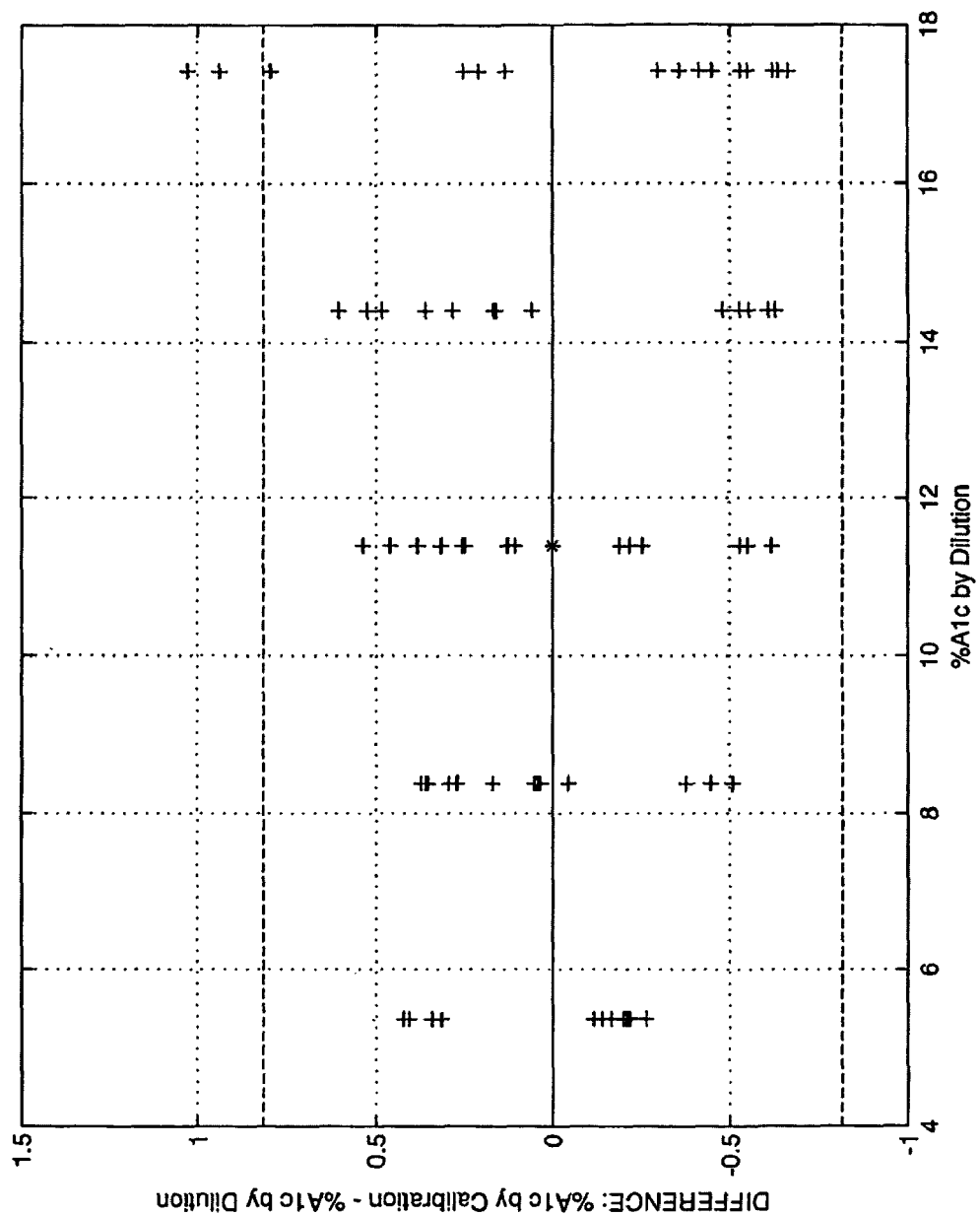
FIG. 6c is a difference plot corresponding to FIG. 6a, in which the difference between the determined $\%A_{1c}$ value and the known value is plotted against the known value.

FIG. 6c is a difference plot in which the difference between the determined value and the known value are plotted against the known value. The known value is determined from the sequence of dilutions used to prepare the data set. While the absolute value may not be accurate, the inaccuracy in the relative values is determined only by inaccuracies in the dilutions. The two dashed lines horizontal lines are 1.96 standard deviations from the mean. This mean, referred to as bias in Table 2, is negligibly different from 0.

Variation 2: Linear in $x_1$, No $x_2$ Dependence With Transformation of Variables A=[1, 0, 5; 1.2, −42, 0] B=[1.2, −42, 0; 0 ,0 ,0]
Model=[0,0; 1,0]
Coefficients=[1.574; 553.816].
for Scale A=1 and Scale B=1.

Figure 7A:
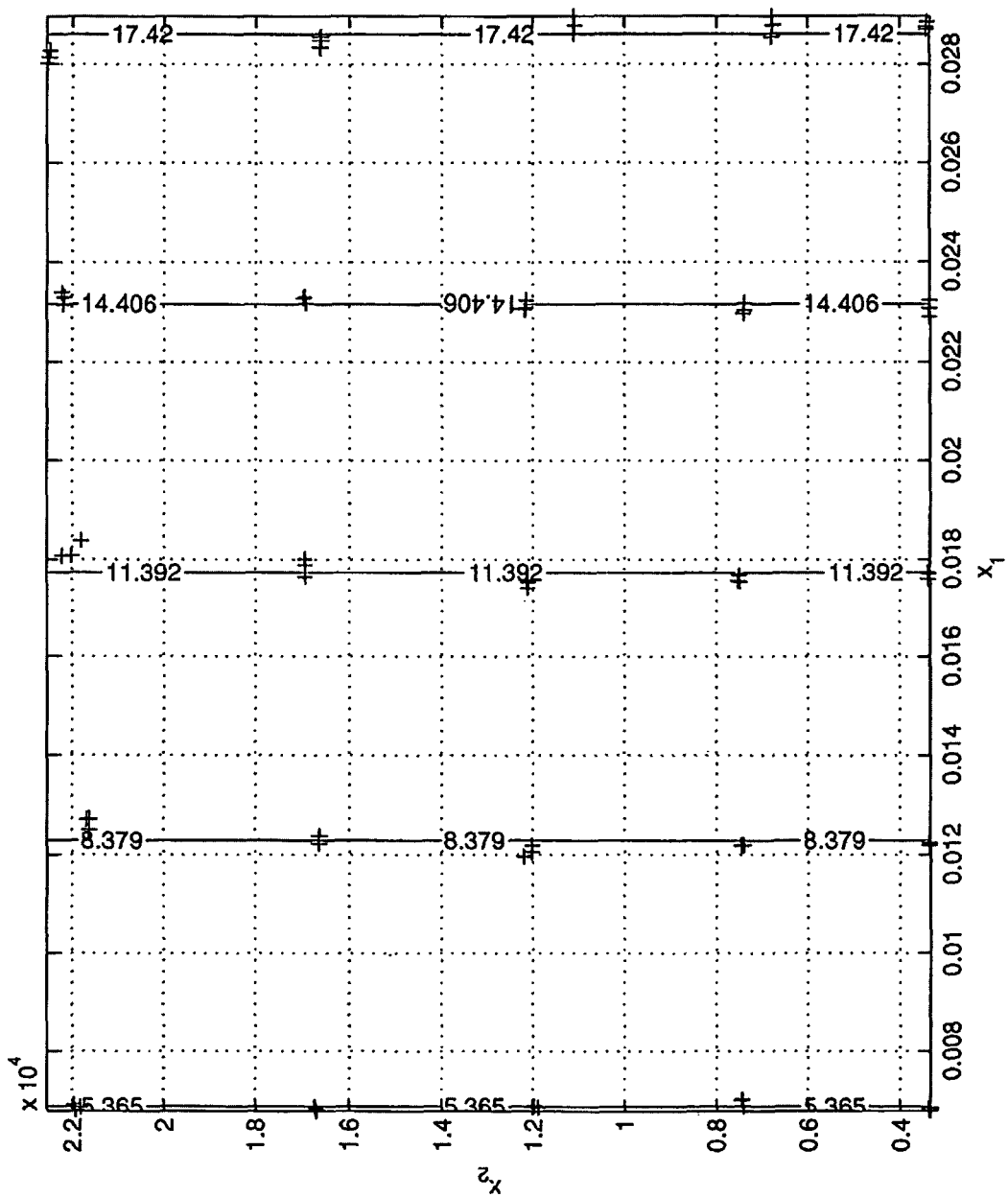
FIG. 7a is a contour plot giving a representation of the calibration surface for Variation 2 of the application of the Calibration Surface method to responses obtained by HPLC.
Figure 7B:
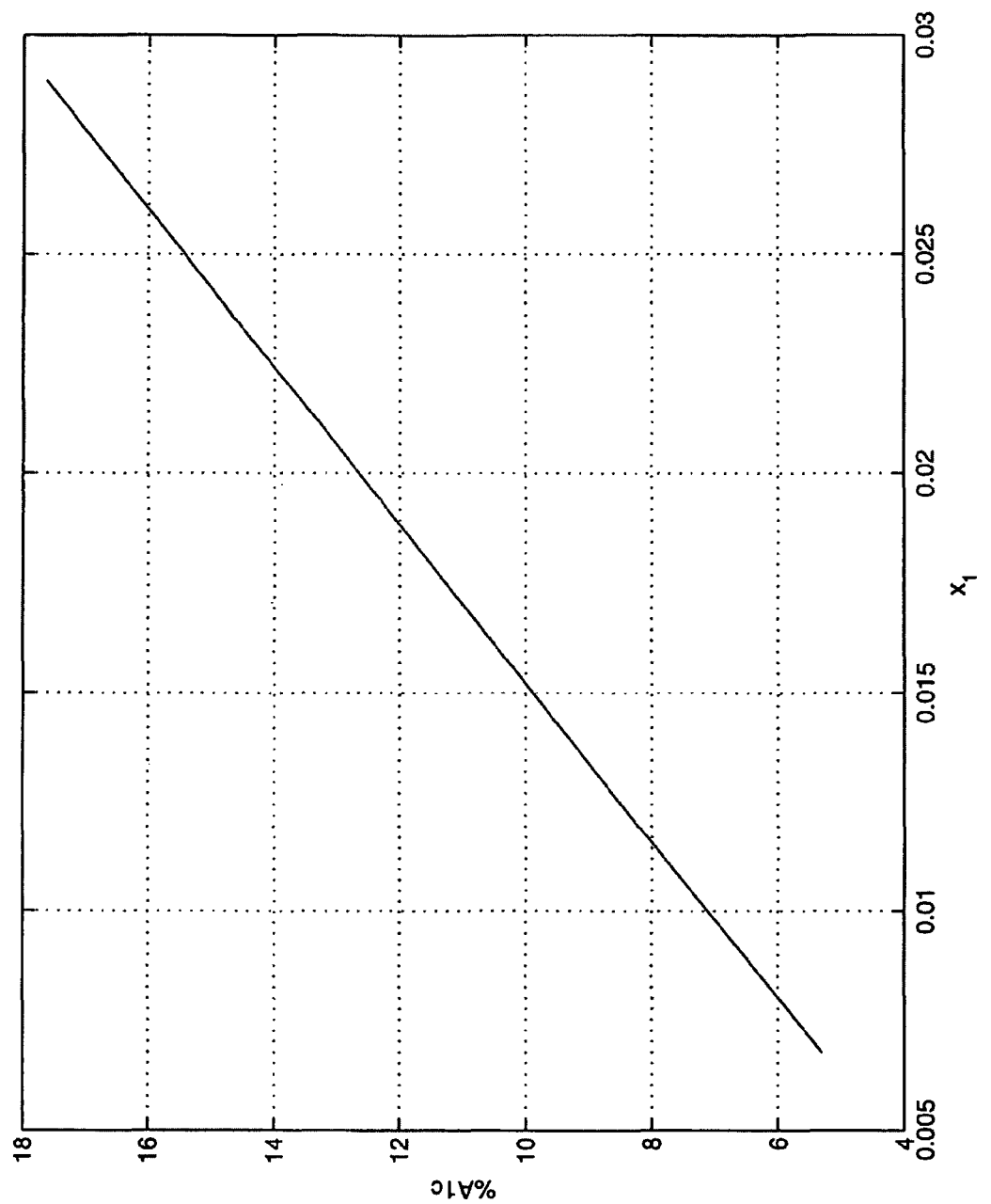
FIG. 7b is a parametric representation of the Calibration Surface of FIG. 7a. Independence from the parameter value results in a single line.
Figure 7C:
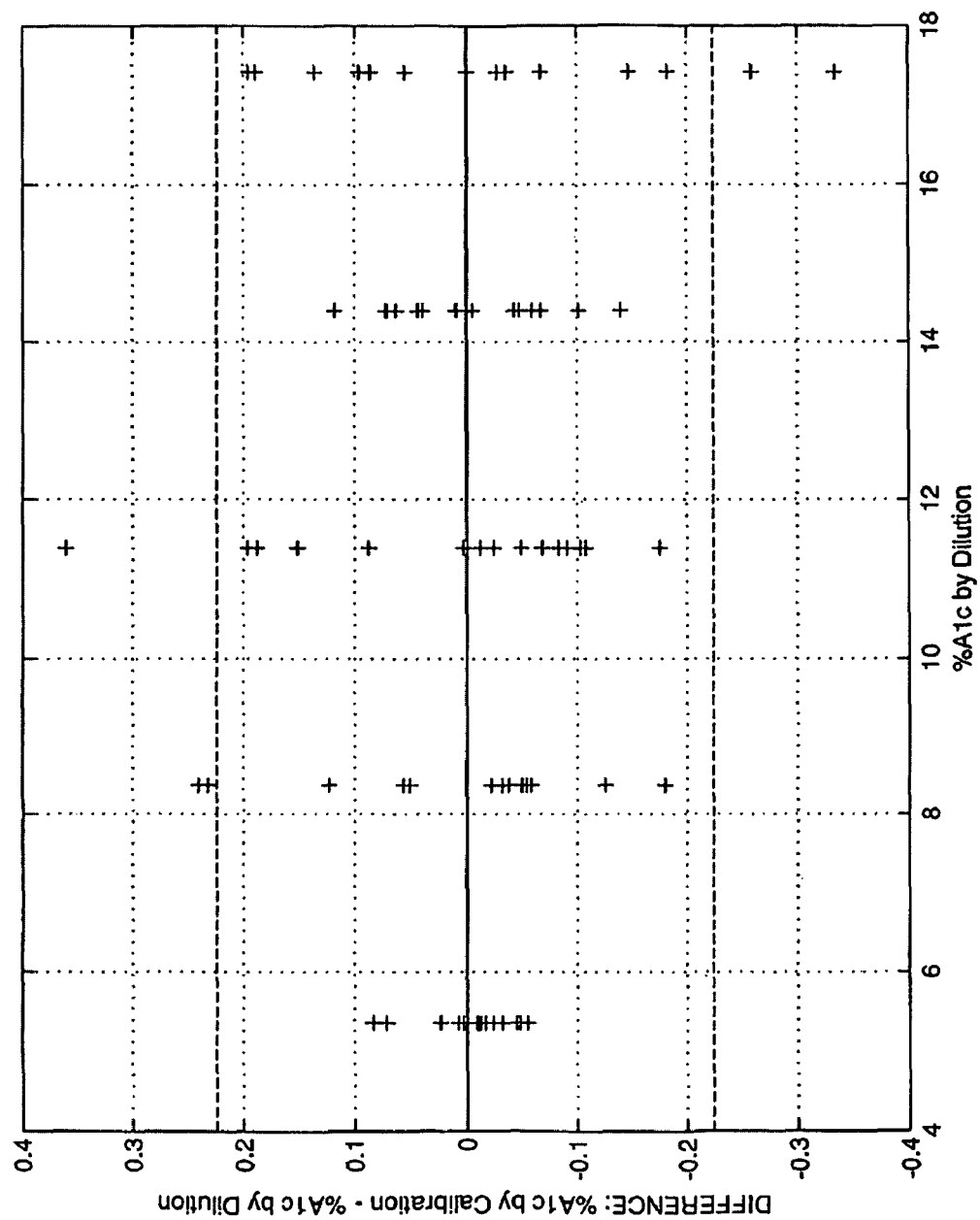
FIG. 7c is a difference plot corresponding to FIG. 7a, in which the difference between the determined $\%A_{1c}$ value and the known value is plotted against the known value.

FIG. 7a is a contour plot and FIG. 7b is a parametric plot of the resulting calibration surface. Since the response is linear in $x_1$ and there is no $x_2$ dependence, this parametric plot reduces to a single straight line. FIG. 7c is a difference plot as described for FIG. 6c.

Variation 3: Linear in $x_1$, Linear in $x_2$ With Transformation of Variables

A=[1,0,0; 1,0,0] B=[1,0,2500; 0,0,0]
Model=[0,0; 1,0; 0,1; 1,1]
Coefficients=[1.2382; 116.3012; 0.1061; −19.7321]
for Scale A=1 and Scale B=2500.

Figure 8A:
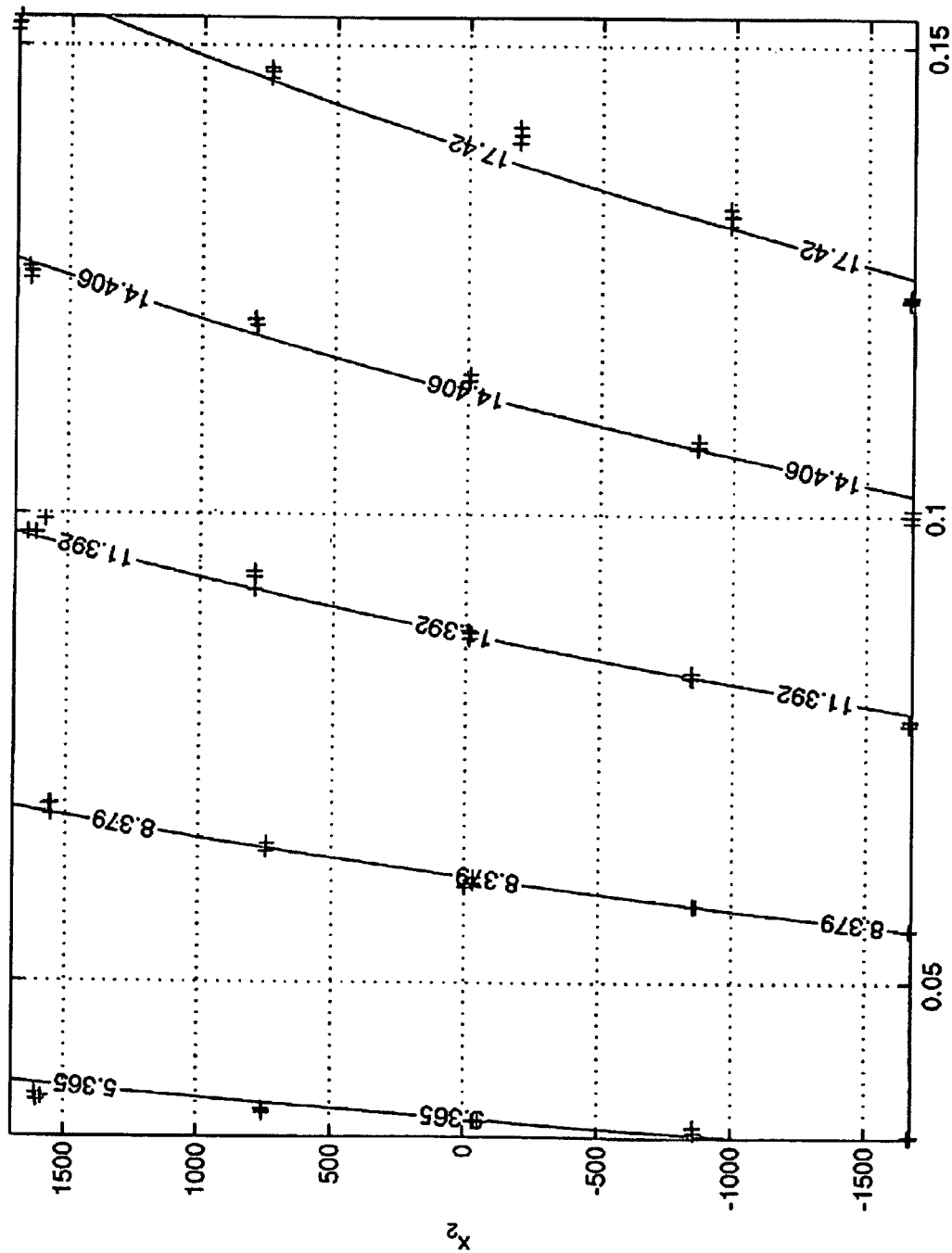
FIG. 8a is a contour plot giving a representation of the calibration surface for Variation 3 of the application of the Calibration Surface method to responses obtained by HPLC.
Figure 8B:
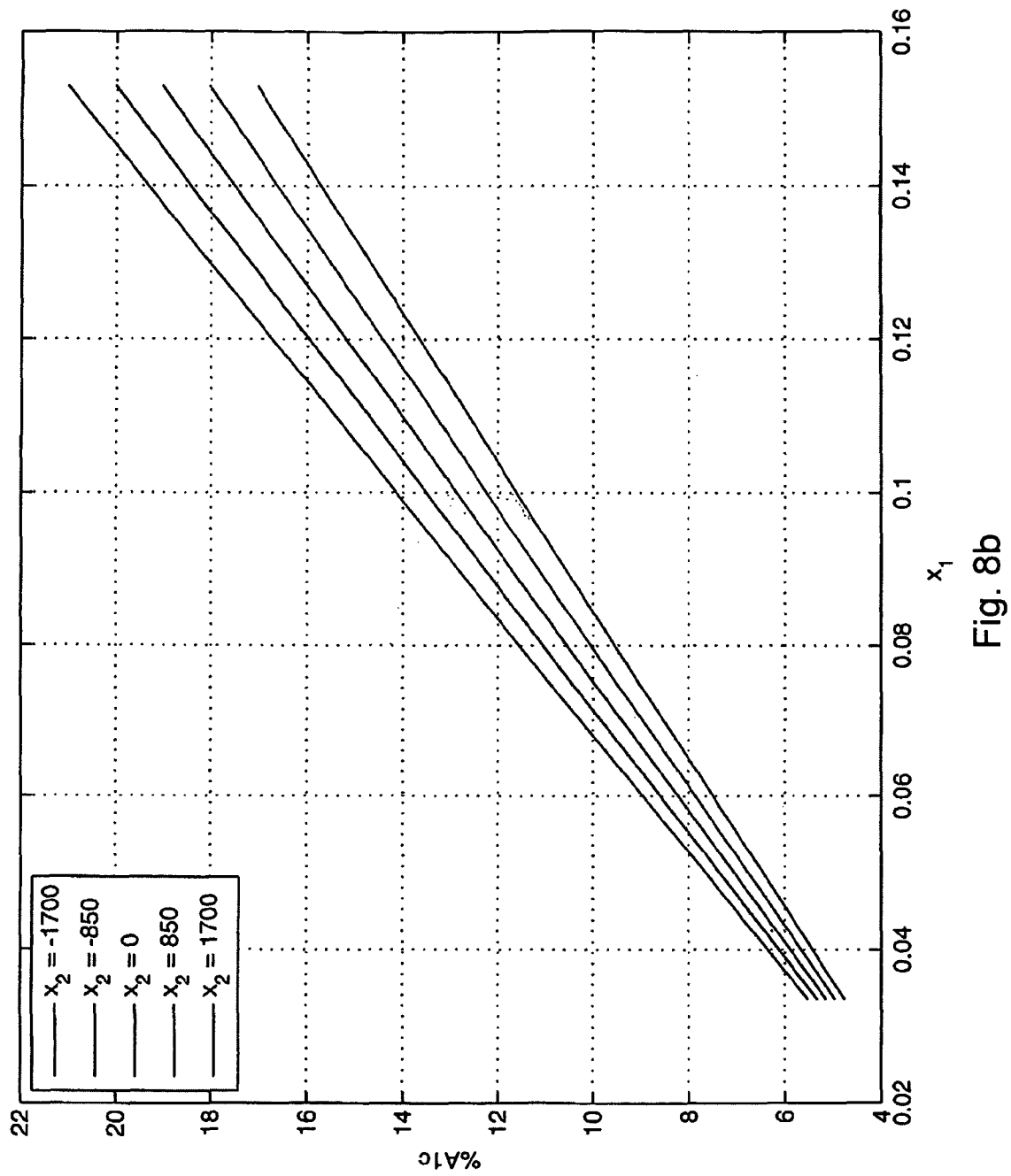
Figure 8C:
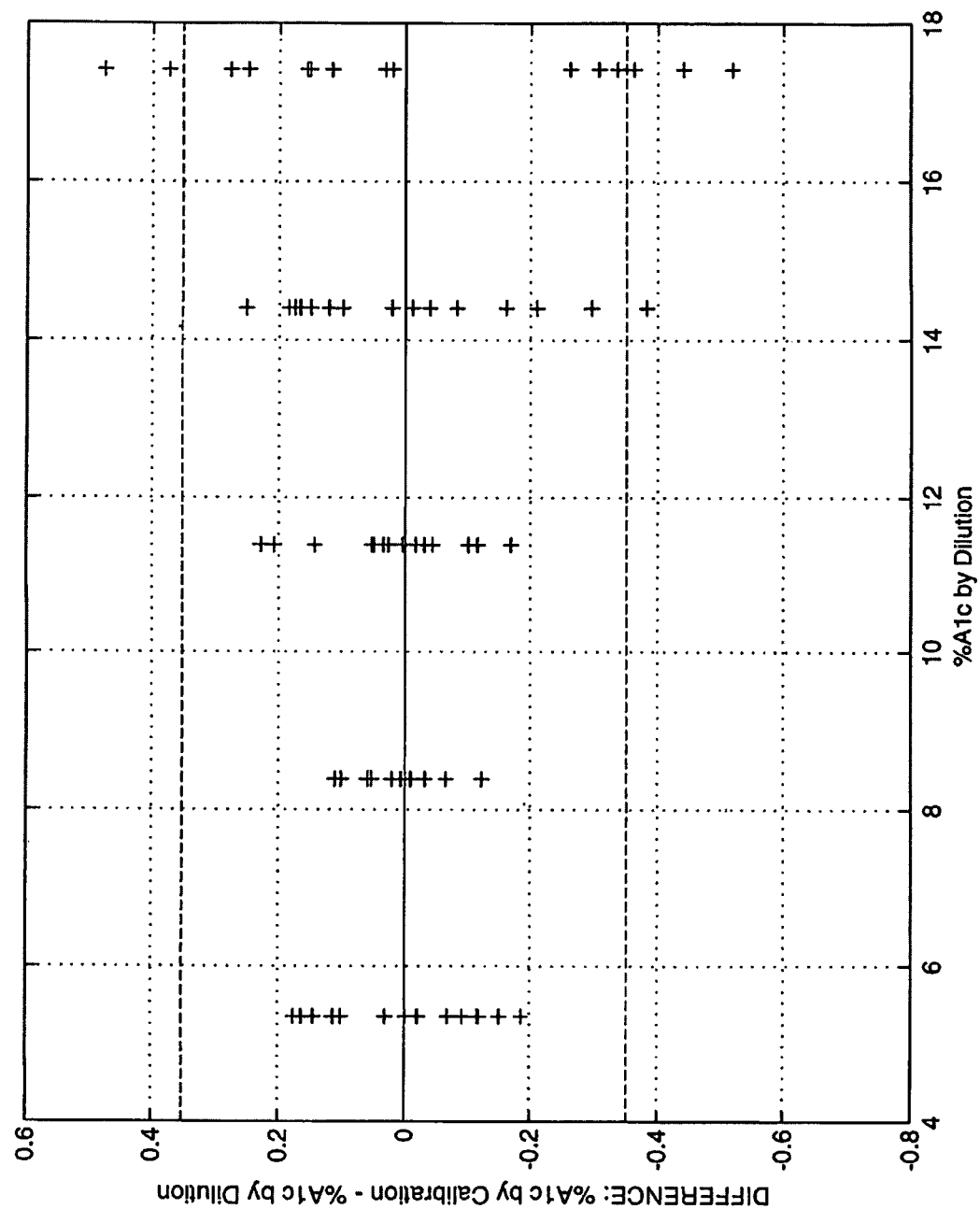
FIG. 8c is a difference plot corresponding to FIG. 8a, in which the difference between the determined $\%A_{1c}$ value and the known value is plotted against the known value.

FIG. 8a is a contour plot and FIG. 8b is a parametric plot of the resulting calibration surface. Since the model is linear in $x_1$, the lines in FIG. 8b corresponding to different values of $x_2$ are straight. From top to bottom, the legend values in FIG. 8b are in the same order as the lines. Linearity in $x_2$ results in equal spacing between lines for the same value of $x_1$. The cross term, $x_1 x_2$, allows the lines to converge as $x_1$ decreases. FIG. 8c is a difference plot as described for FIG. 6c.

In variation 3, the values of A and B result in $x_1$=HbGr/HbTr and $x_2$=HbTr−2500. The first transformation defines $x_1$ as the ratio of the responses and the second transformation puts $x_2$=0 at the center of the expected range of values of HbTr. This latter transformation is merely for convenience.

Variation 3 illustrates how the model coefficients can be divided into coefficients that are determined on different time intervals. The transformation coefficients, represented in matrixes A and B, can be set during the development of the method and do not have to change thereafter. The four model parameters can be calibrated by the reagent manufacturer for different lots of reagents. The first two coefficients could then be calibrated by laboratory on a shorter interval using only two calibrators. The calibrators would preferably have an HbTr response near the mid range value of 2500. However, any differences from that value could be accommodated by using the current coefficient values to adjust the labeled value of the calibrator to a value corresponding to HbTr=2500, which corresponds to $x_2=0$.

The following equations illustrate this technique.

The first equation of the model can be re-written as $$K = K_0 + \beta_{01} x_2 + \beta_{11} x_1 x_2 \quad (1)$$

in which K is the known value of % $A_{1c}$ for calibration (determination of the coefficients) and the determined value of % $A_{1c}$ when (1) is applied with known coefficients.
and $$K_0 = \beta_{00} + \beta_{10} x_1 \quad (2)$$

During calibration, the known values are adjusted to the values they would have for $x_2=0$, by the equation, derived from (1)

$$K_0 = K - \beta_{01} x'_2 + \beta_{11} x'_1 x'_2 \quad (3)$$

In which $x'_1$ and $x'_2$ are the new transformed response which differs from $x_1$ and $x_2$ because of changes in the system since the time that the unprimed values were determined.

Using two (or more) known values of K, (3) is solved for $K_0$. These $K_0$ values are substituted into (2) to create simultaneous equations from which new values of $\beta_{00}$ and $\beta_{10}$ are determined. Using primes to distinguish these new values, (2) can be written as $$K_0 = \beta'_{00} + \beta'_{10} x'_1 \quad (4)$$

Equating the right-hand side of (2) and (4) gives a linear relationship between $x_1$ and $x'_1$.

$$x_1 = \frac{\beta'_{00} - \beta_{00}}{\beta_{10}} + \frac{\beta'_{10}}{\beta_{10}} x'_1 \quad (5)$$

Equation (5) is a linear estimation to the actual relationship between $x_1$ and $x'_1$ if the same samples were measured under the current conditions when the primed parameters are determined and the original conditions when the unprimed parameters were determined.

The updated equation for determining % $A_{1c}$ is $$\% A_{1c} = \beta'_{00} + \beta'_{10} x'_1 + \beta_{10} x_2 + \beta_{11} x_1 x_2 \quad (6)$$

in which $x_1$ is determined from $x'_1$ by (5).

If no better relationship between $x_2$ and $x'_2$ is known then the two can be equated for use in (6).

$$x_2 = x'_2 \quad (7)$$

For conditions which change such that there is a linear relationship between the original and current values of $x_1$ and no change between the original and current values of $x_2$, (5), (6) and (7) accurately reflect the change. In practice, the linear relationship may not hold and the terms in (6) containing $x_2$ represent a small correction factor. Changes in % $A_{1c}$ are, thus, not sensitive to small changes in $x_2$, especially when the magnitude of $x_2$ is small.

For those skilled in the art, various improvements can be made to this illustration. For example, iteration could be used. Once the new primed coefficients are determined, they can be substituted into (3) for the unprimed coefficients and the remaining steps repeated to refine the results.

Variation 4: Linear in $x_1$, $2^{nd}$ Order $x_2$ Dependence With Transformation of Variables A=[1,0,0; 1,0,0] B=[1,0,2500; 0,0,0]
Model=[0,0; 1,0; 0,1; 1,1; 1,2]
Coefficients=[1.2400; 114.6677; 0.2489; −21.4608; 7.6198]
for Scale A=1 and Scale B=2500.

Figure 9A:
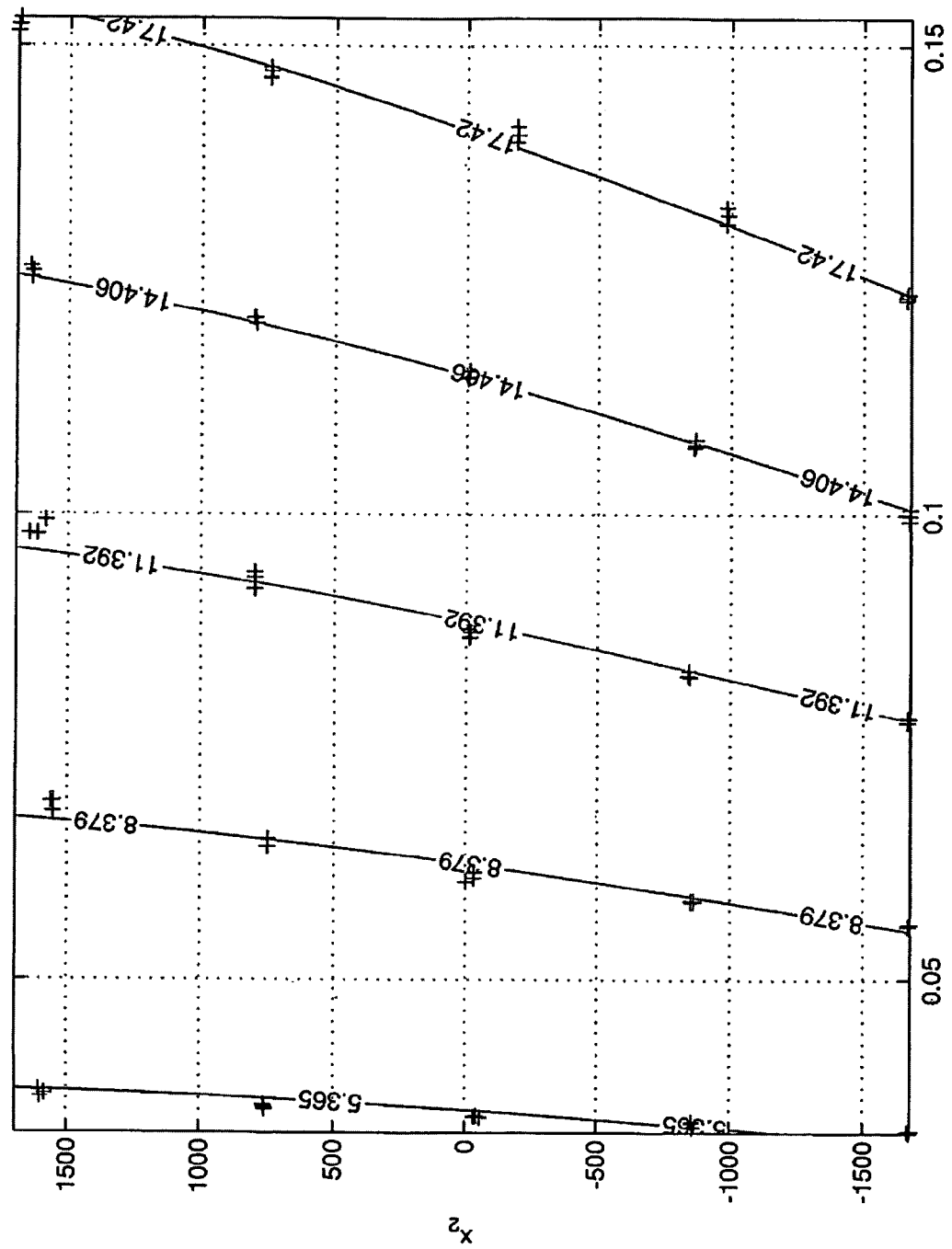
FIG. 9a is a contour plot giving a representation of the calibration surface for Variation 4 of the application of the Calibration Surface method to responses obtained by HPLC.
Figure 9B:
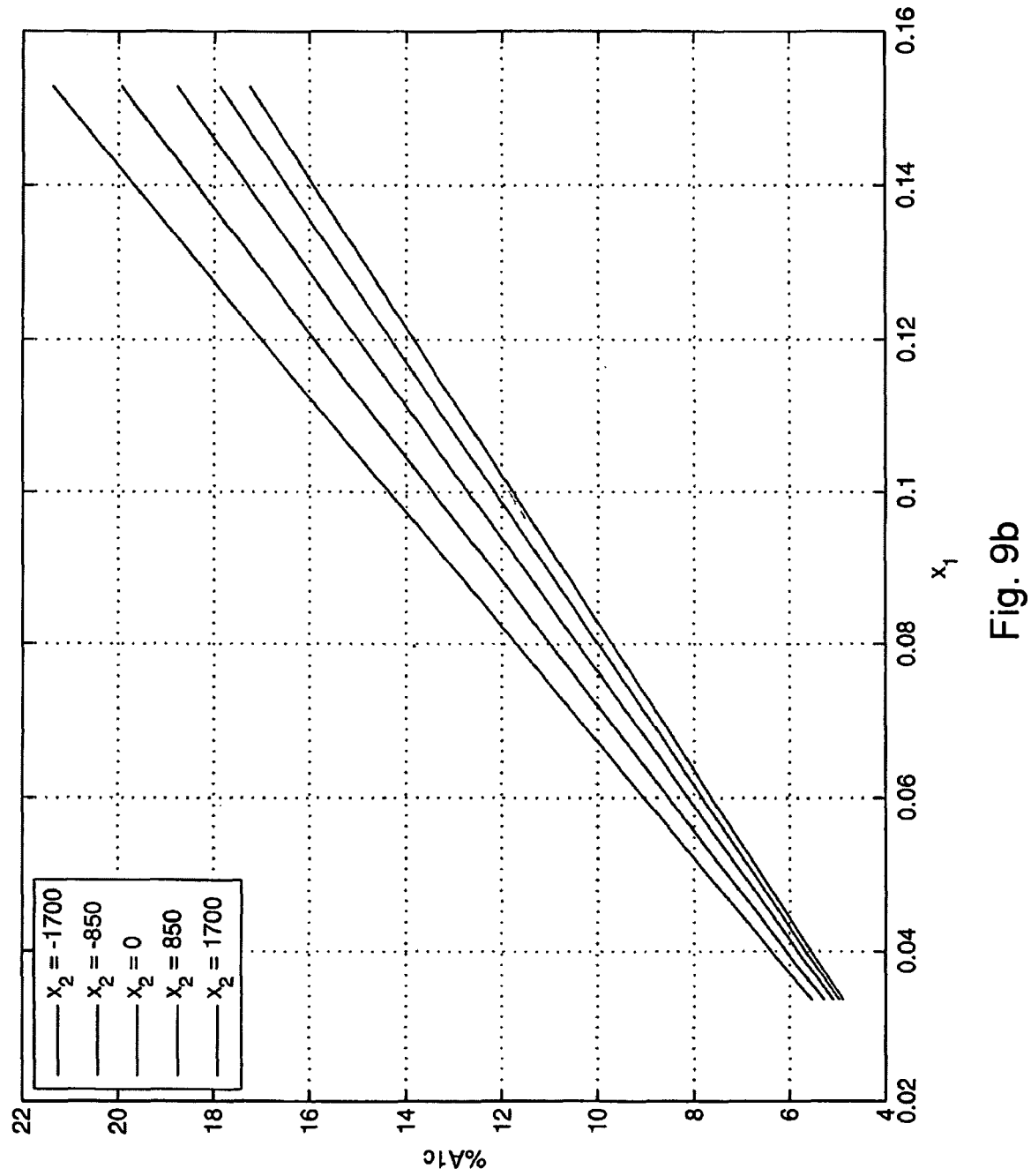
Figure 9C:
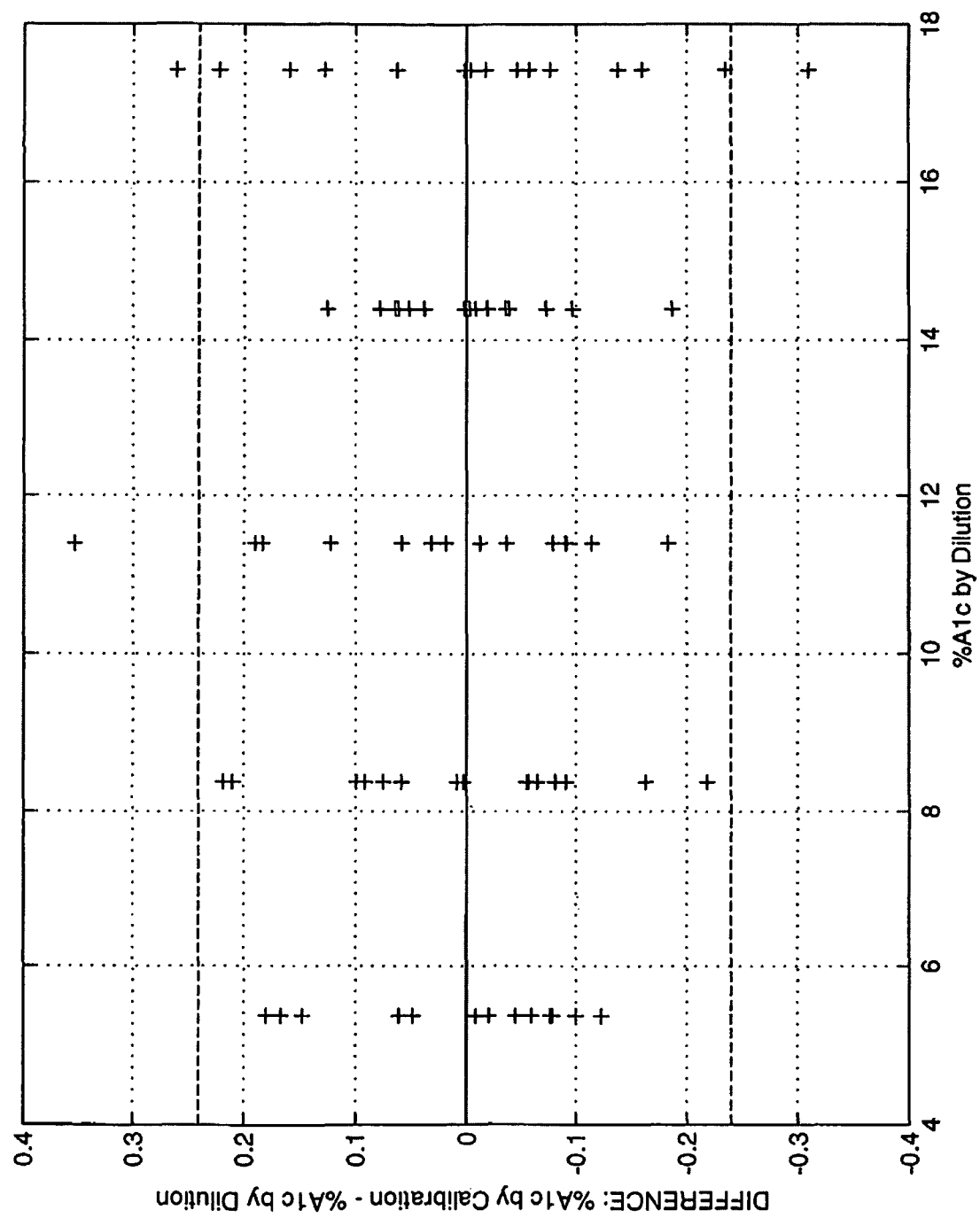
FIG. 9c is a difference plot corresponding to FIG. 9a, in which the difference between the determined $\%A_{1c}$ value and the known value is plotted against the known value.

FIG. 9a is a contour plot and FIG. 9b is a parametric plot of the resulting calibration surface. The addition of the $x_1 x_2^2$ term allows the spacing of the straight lines in FIG. 9b to be different for different pairs of $x_2$ values. From top to bottom, the legend values in FIG. 9b are in the same order as the lines. FIG. 9c is a difference plot as described for FIG. 6c. The additional term in the model reduces the lack-of-fit, LOF, error as can be seen by comparing FIG. 8c and FIG. 9c at the expense of introducing extra complexity into the model. Since there are still only two terms that do not contain $x_2$, only two calibrators are needed for short term calibration. The long term stability of the model may, however, be compromised by the additional complexity.

An illustrative example following the form of that given for Variation 3 could also be given for this variation.

Analysis of Components of Variance

Table 2 is a compilation of the Components of Variance for the four variations presented in the preceding sections. In the table, LOF is an abbreviation for lack-of-fit and Replicate is a component of variance determined from the differences in replicate responses. It is also referred to as Pure Error.

TABLE 2

| Component | Variation 1 | Variation 2 | Variation 3 | Variation 4 |
| --- | --- | --- | --- | --- |
| LOF for % A1c | negligible | negligible | negligible | negligible |
| LOF for HbTc | 0.205139 | 0.011589 | 0.034847 | 0.0141014 |
| Replicate | 0.005328 | 0.003738 | 0.003835 | 0.003736 |
| Total Corrected | 0.173475 | 0.012869 | 0.032115 | 0.015009 |
| Bias | negligible | negligible | negligible | negligible |
| Total Uncorrected | 0.171162 | 0.012869 | 0.031687 | 0.014809 |

Variation 1 has a higher replicate error then the other three variations. Variations 3 and 4 use a ratio of responses for variable 1 which cancels much of the error common to both responses. This common error could result from differences in the sample size used for the replicates. The lack-of-fit variance for different values of % $A_{1c}$ was negative and thus reported as negligible. The lack-of-fit error for different values of the total hemoglobin concentration, HbTc, was the most significant factor. Variation 1 is not only complex, but it has the largest value for this error. Variation 3 has a significantly smaller error and because of its simplicity, it might be favored over Variations 4 and 2, which are more complicated.

The bias for all variations was less than $10^{-12}$ and thus reported as insignificant. This low value is inherent in auto-calibration in which the same samples are used as calibrators and patient samples. Because of this low values, the ratio of the total uncorrected variance to the total corrected variance is simply the inverse of the ratio of their associated degrees of freedom, 74/75, since there was a total of 75 samples.

These four variations are presented for illustrative purposes. Other variations may be more appropriate for this HPLC data set and/or a different HPLC data set.

Multi-Analyte Immunoassay Method for Measuring HbA1c

Another embodiment of the proposed method uses a multi-analyte immunoassay method for measuring HbA1c.

Figure 4A:
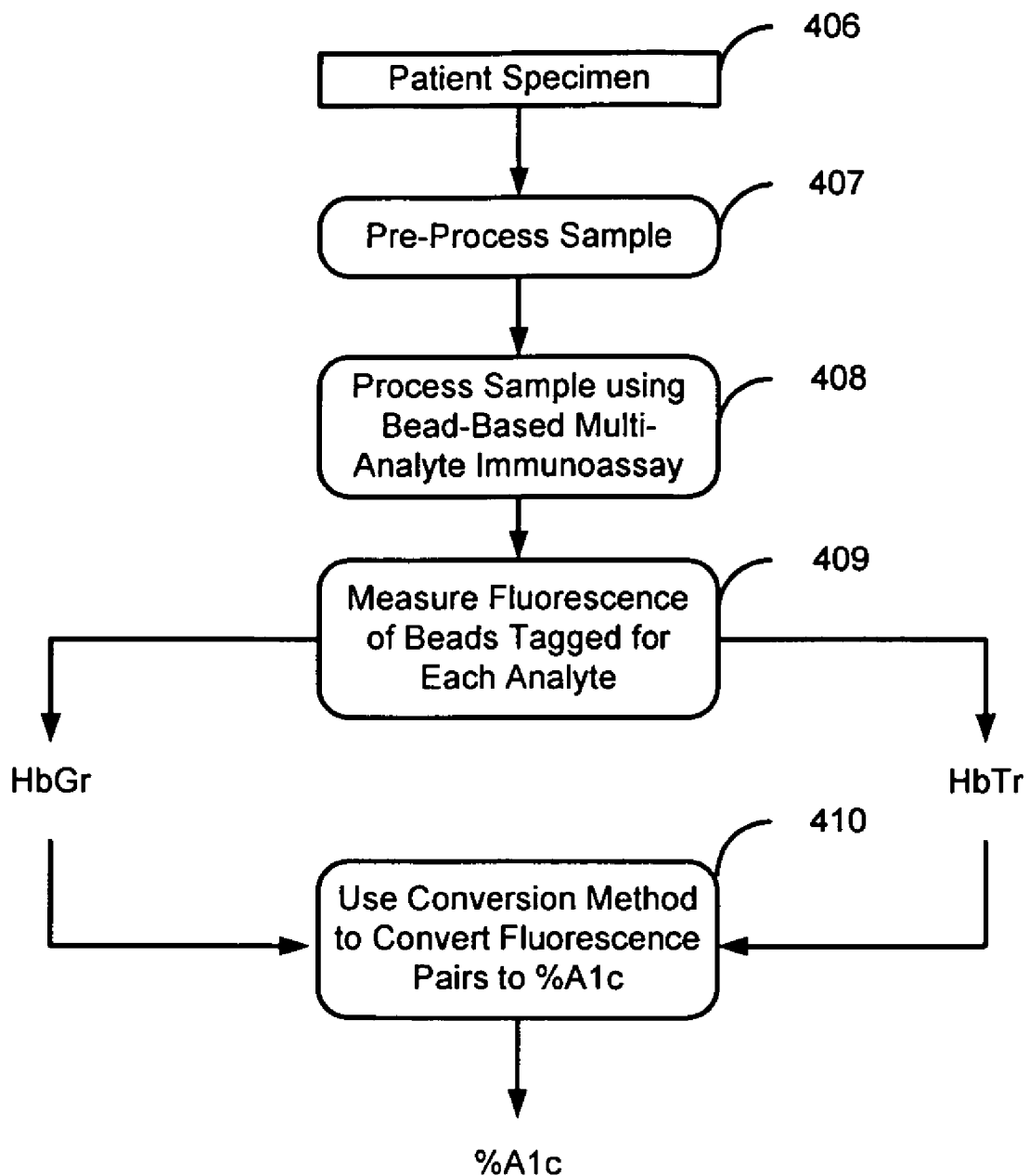
FIG. 4a is a flow chart depicting the proposed method for calculating % A1c through a multi-analyte immunoassay measurement method.

FIG. 4a illustrates the steps involved in calculating the ratio of HbA1c to total hemoglobin according to a multi-analyte immunoassay method of measuring HbA1c.

Steps 406-409 are essentially identical to steps 101-104 displayed in FIG. 1 and steps 201-204 in FIG. 2. At step 406, a patient specimen is obtained. At step 407, this patient specimen is converted into a pre-processed or test sample and at step 408, a multi-analyte immunoassay is used to produce a population of labeled beads in which the ratio of beads labeled as glycosylated hemoglobin (HbG) beads to those labeled as total hemoglobin (HbT) beads is related to the concentration of glycosylated (HbGc) and total hemoglobin (HbTc). These beads have antibodies to HbG and HbT and corresponding fluorescent tags that allow them to be identified as HbG or HbT beads. They also contain another distinct fluorescent tag that allows them to be quantified. Reading of theses beads for identity and quantity is step 409. This reading is accomplished by flowing the beads past two lasers that excite the beads to fluoresce in different colors for identification and quantifying. The amount of quantifying fluorescence from the beads identified as HbG and HbT beads are shown as "HbGr=Fluorescence from Beads with HbG Antibodies" and "HbTr=Fluorescence from Beads with HbT antibodies."

A 9×9×3 sample set was used to generate a data set. Since the highest level of % A1c demonstrated a significant amount of saturation it was not used. The sample set was thus reduced to an 8×9×3 sample set. In addition to some remaining saturation at the highest remaining % A1c level, this sample set had somewhat more than twice the replicate error compared with the HPLC data set. In addition to the non-linearities inherent in immunoassays, the data exhibits cross-reactivity between the antibody for one member of the pair and the concentration of the other member. Two variations of the application of the Calibration Surface method will be presented for this data set. The variations will be called Variation 5 and Variation 6. The same definitions and formats used to present the HPLC data will be used. Because of the large amount of raw data, it is not be presented as a table. However, an Analysis of Components of Variance table is presented.

Variation 5: Model Contains 6-terms and $x_1$=HbGr/HbTr
A=[1, 0, 0; 1, 0, 0] B=[1, 0, 0; 0, 0, 0]
Model=[0,0; 1,0; 2,0; 0,2; 2,1; 1,2]
Coefficients=[4.1202; 9.5793; −1.8632; −0.5667; 1.1353; −0.6738]
for Scale A=1 and Scale B=10000.

Figure 10A:
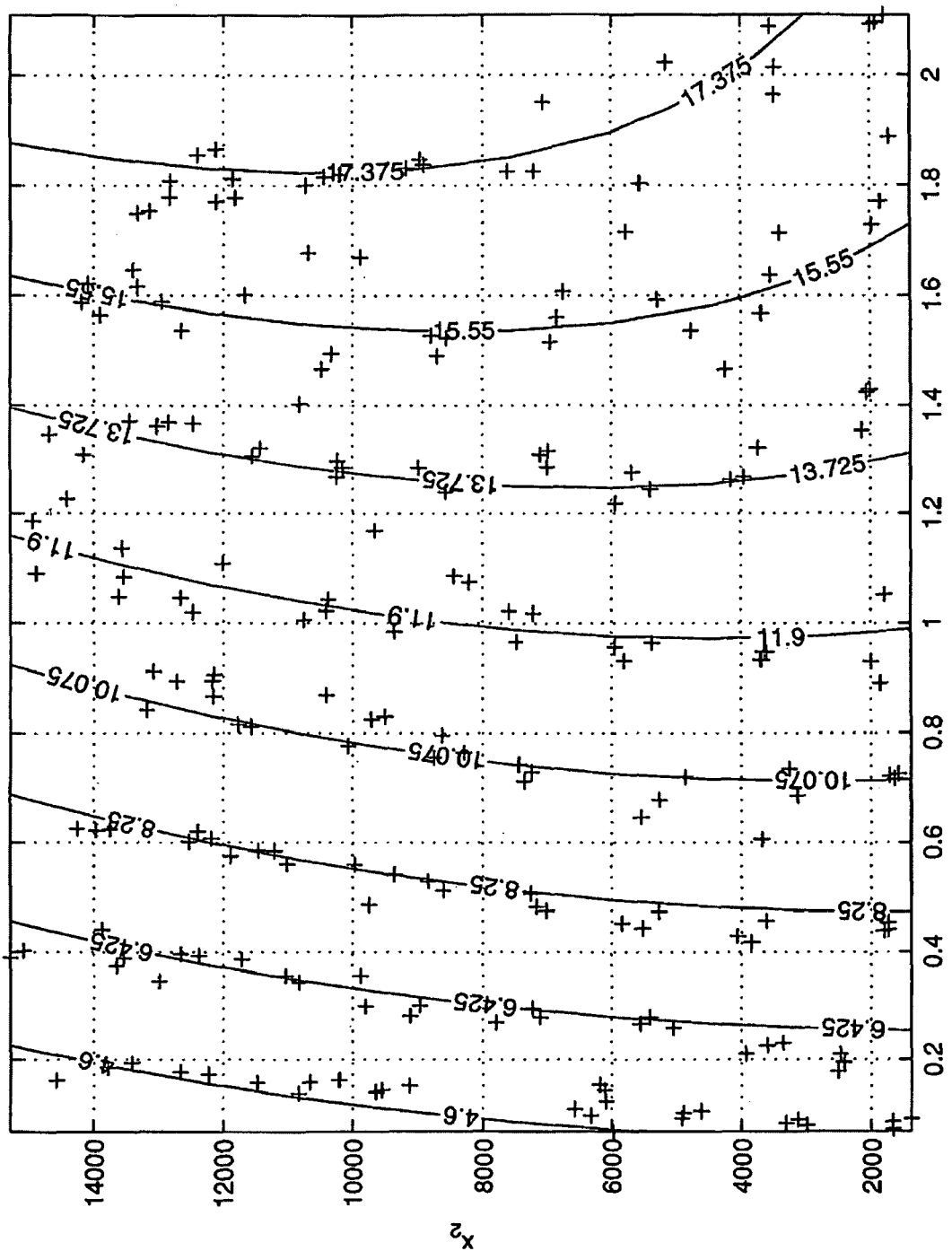
FIG. 10a is a contour plot giving a representation of the calibration surface for Variation 5 of the application of the Calibration Surface method to responses obtained by a multi-analyte immunoassay.
Figure 10B:
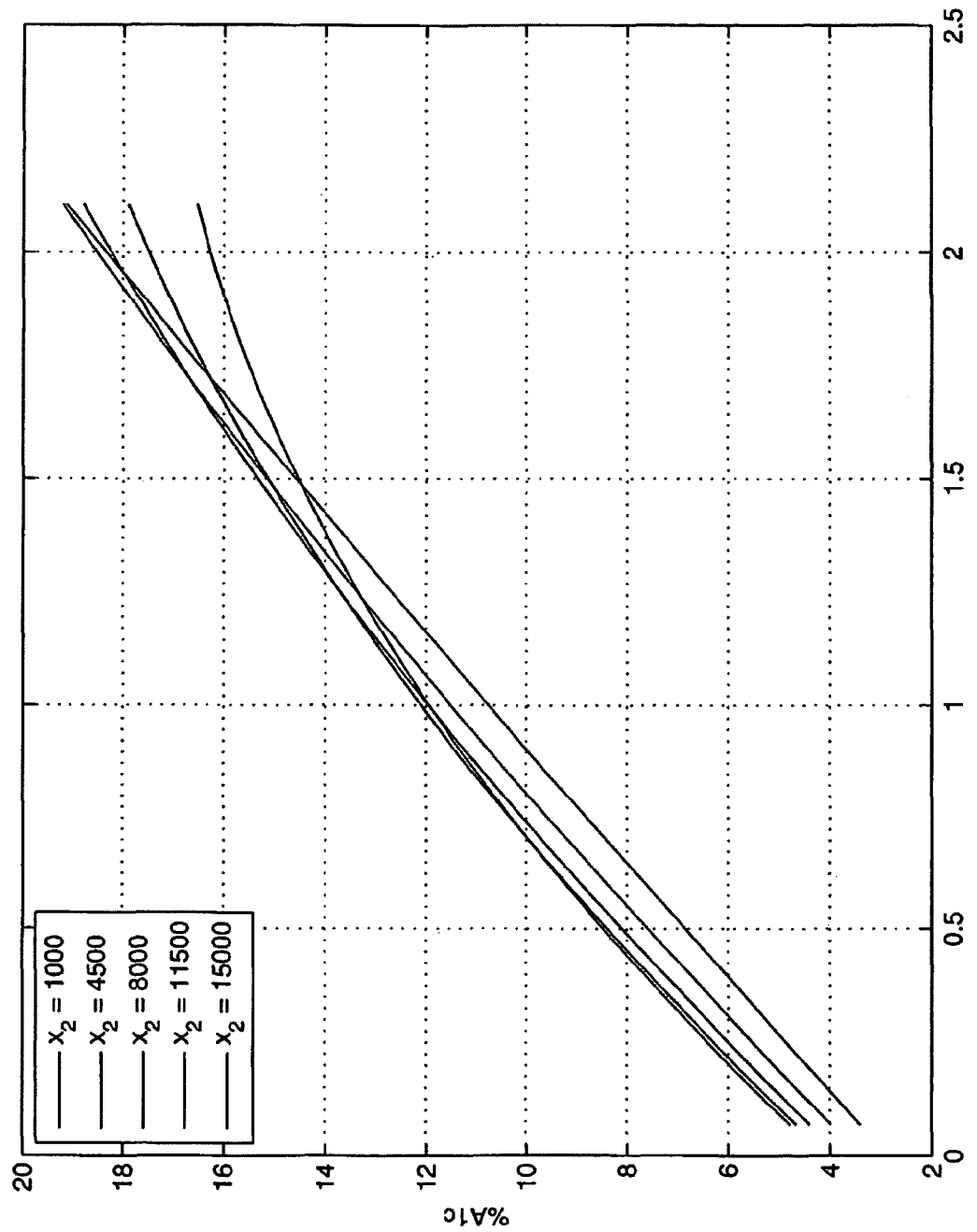
Figure 10C:
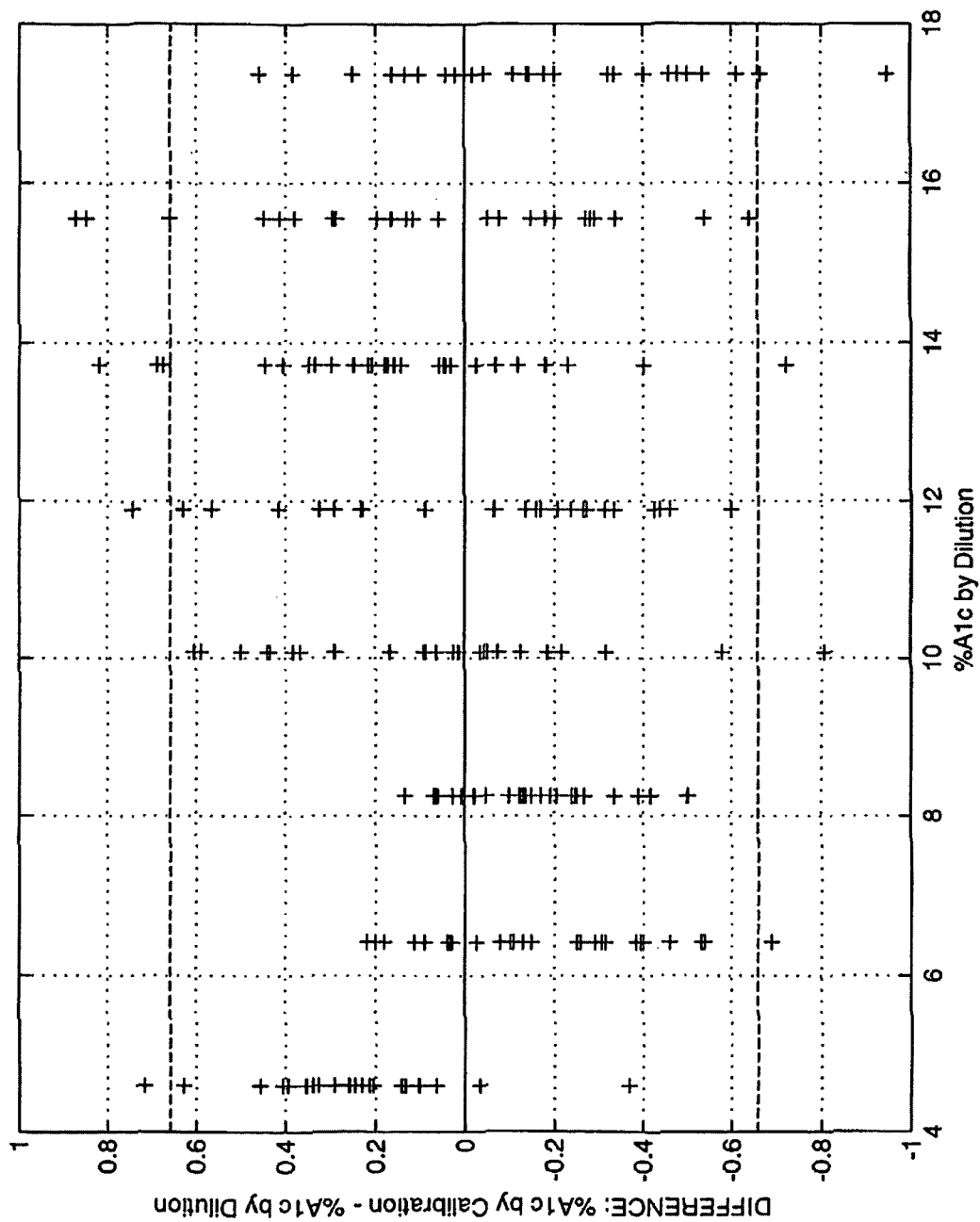
FIG. 10c is a difference plot corresponding to FIG. 10a, in which the difference between the determined $\%A_{1c}$ value and the known value is plotted against the known value.

FIG. 10a is a contour plot and FIG. 10b is a parametric plot of the resulting calibration surface. From top to bottom, the legend values in FIG. 10b are in the same order as the curves for values of $x_1$ less than 0.5. FIG. 10c is a difference plot in which the difference between the determined value and the known value are plotted against the known value which is determined by dilution. The two dashed lines horizontal lines are 1.96 standard deviations from the mean.

Variation 6: Transforms Make Model Linear in $x_1$ and $x_2$
A=[0.75, 0, 36; 1.5, 0, −500] B=[0.93, 0, 0; 0, 0, 0]
Model=[0,0; 1,0; 0,1; 1,1]
Coefficients=[5.4077; 0.8364; −5.4188; 52.9571]
for Scale A=0.003 and Scale B=10000.

Figure 11A:
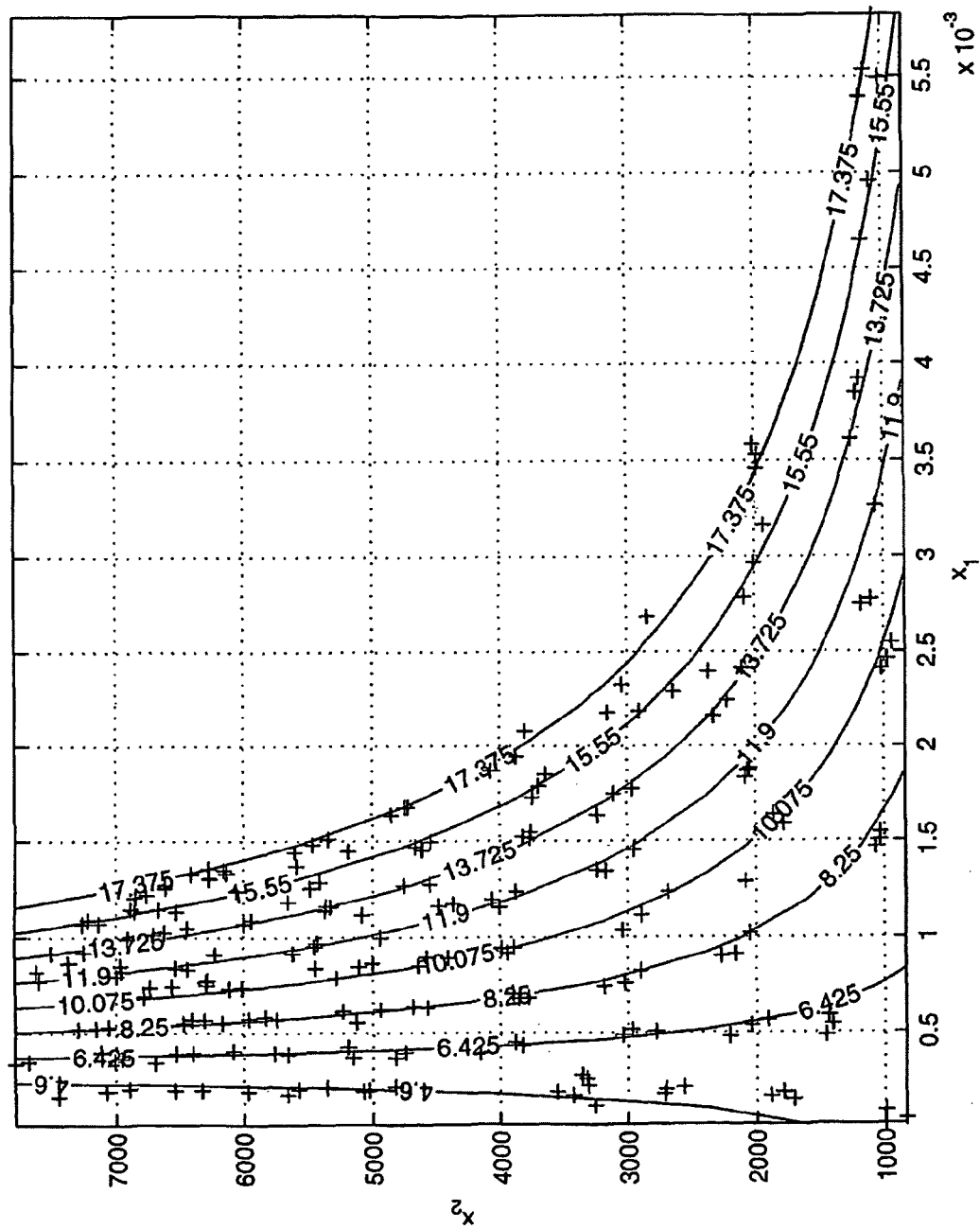
FIG. 11a is a contour plot giving a representation of the calibration surface for Variation 6 of the application of the Calibration Surface method to responses obtained by a multi-analyte immunoassay.
Figure 11B:
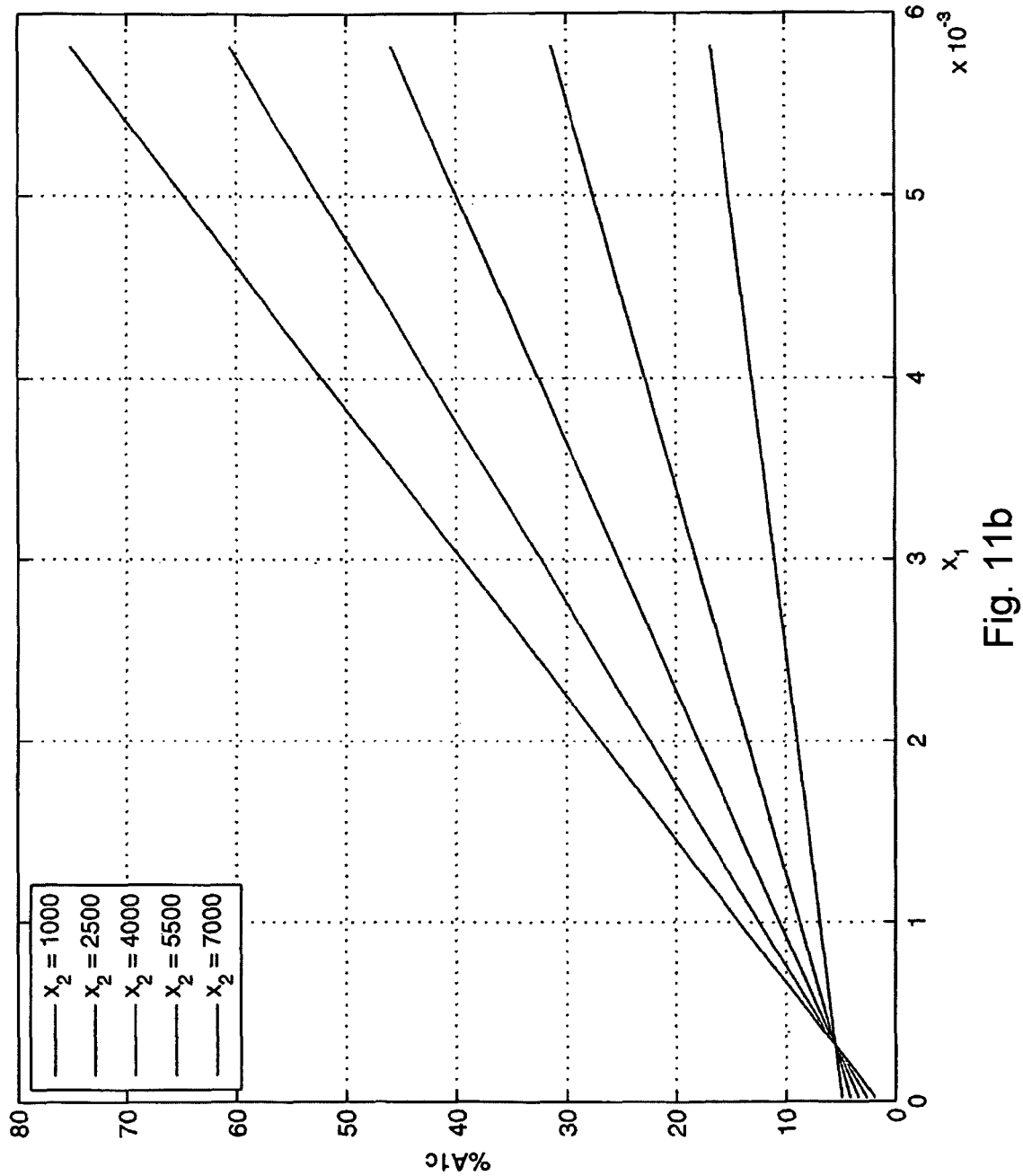
Figure 11C:
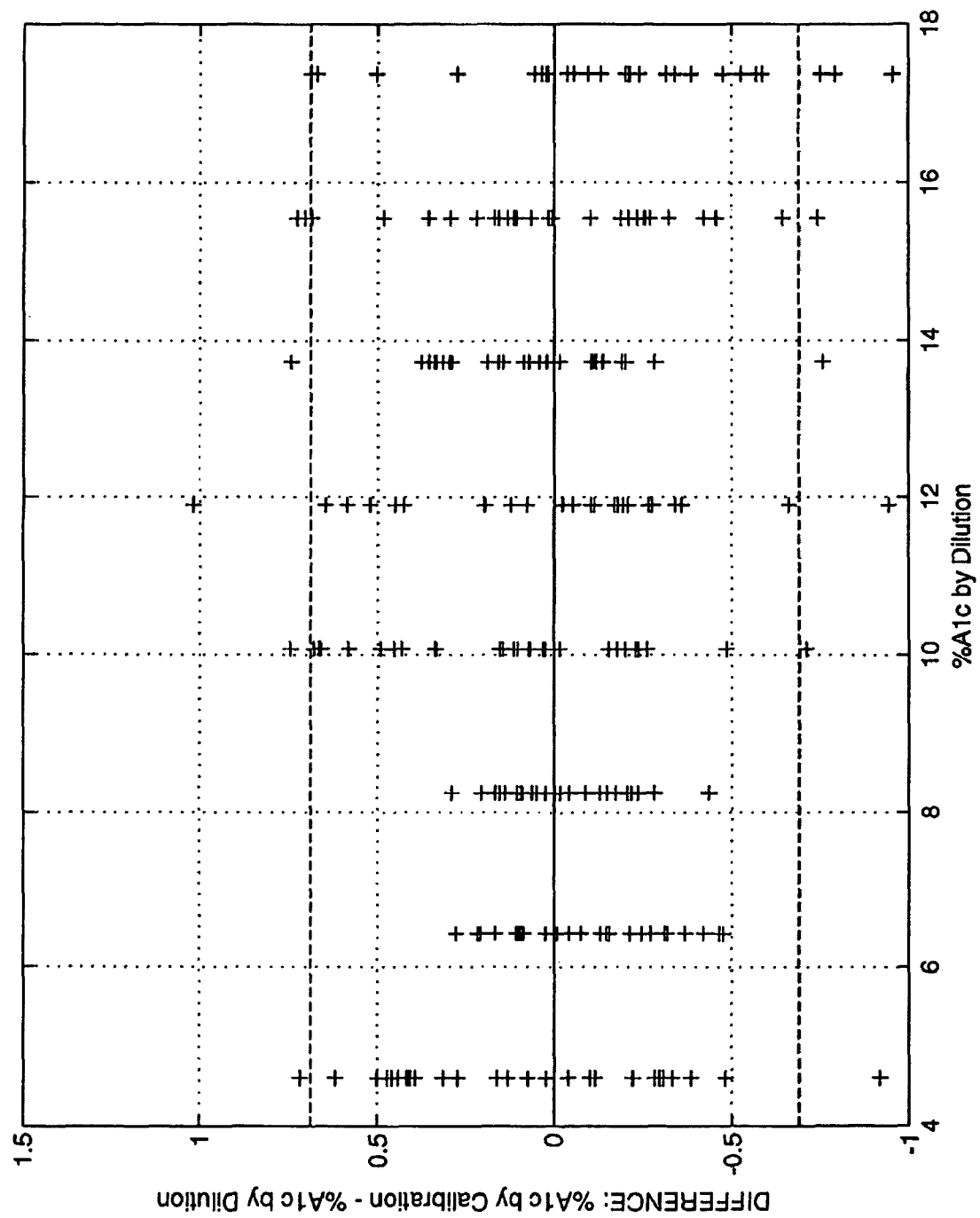
FIG. 11c is a difference plot corresponding to FIG. 11a, in which the difference between the determined $\%A_{1c}$ value and the known value is plotted against the known value.

FIG. 11a is a contour plot and FIG. 11b is a parametric plot of the resulting calibration surface. From top to bottom, the legend values in FIG. 11b are in the same order as the lines for values of $x_1$ less than 0.0003 and in the opposite order for $x_1$ greater than 0.003. The $x_1$ value where all of the lines cross in FIG. 11b corresponds to a vertical contour in FIG. 11a. FIG. 11c is a difference plot in which the difference between the determined value and the known value are plotted against the known value.

Analysis of Components of Variance

Table 3 is a compilation of the Components of Variance for the two variations presented in the preceding sections. The terminology is the same as in Table 2

TABLE 3

| Component | Variation 5 | Variation 6 |
| --- | --- | --- |
| LOF for % A1c | 0.022141 | 0.002226 |
| LOF for HbTc | 0.014924 | 0.042328 |
| Replicate | 0.078614 | 0.080017 |
| Total Corrected | 0.112862 | 0.123908 |
| Bias | negligible | negligible |
| Total Uncorrected | 0.112339 | 0.123335 |

Because the Bias is negligible, the ratio of the total uncorrected variance to the total corrected variance is simply the inverse of the ratio of their associated degrees of freedom, 215/216, since there was a total of 72 samples with 3 replicates.

These two variations give comparable components of variance. They represent two of the many tradeoffs that can be made between the complexity of the model and the complexity of the transformation. Variation 6 achieves linearity in both variables at the expense of having five transformation coefficients in addition to the four model coefficients.

The optimum balance between the model coefficients and the transform coefficients depends on the particular application in which the Calibration Surface is used. Other forms of the general transformation model used to demonstrate these variations may be beneficial. Models in which the variables are used in more complex combinations than used in these variations may also be of advantage and may reduce or eliminate the need for any additional transformation.

A recitation of "a", "an" or "the" is intended to mean "one or more" unless specifically indicated to the contrary.

While the present teachings have been described in terms of these exemplary embodiments, the skilled artisan will readily understand that numerous variations and modifications of these exemplary embodiments are possible without undue experimentation. All such variations and modifications are within the scope of the current teachings. The foregoing examples are provided to better illustrate the disclosed teachings and are not intended to limit the scope of the teachings presented herein.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

What is claimed is:

1. A method for determining a ratio of concentrations of different analytes in a sample, said method comprising:
measuring responses of two or more analytes in a sample using a selected measuring process to obtain two or more individual analyte responses of the two or more analytes;
selecting one or more conversion methods that define a ratio of the concentrations of the two or more analytes as a direct function of the two or more individual analyte responses obtained using the selected measuring process, wherein the direct function includes a multi-variable regression model that outputs the ratio of the concentrations, and wherein the multiple variables of the regression model include the two or more individual analyte responses; and computing, with a processor, the ratio of the concentrations of the two or more analytes in the sample using the selected one or more conversion methods and using the two or more individual analyte responses.

2. The method of claim 1 wherein the ratio output from the direct function is defined as the concentration of one analyte divided by the concentration of another analyte.

3. The method of claim 1 wherein the direct function relates the measured individual analyte responses to the ratio of the analytes using the multi-variable regression model with the measured individual analyte responses as regression variables.

4. The method of claim 1 wherein the multi-variable regression is a polynomial regression in which the variables are products of the analyte responses raised to integer powers.

5. The method of claim 3 wherein the two or more individual analyte responses used in the one or more conversion methods undergo a transformation as a part of one or more conversion methods.

6. The method of claim 5 wherein the transformation reduces the number of regression terms used in the regression model.

7. The method of claim 5 wherein the transformation facilitates a longer laboratory calibration interval.

8. The method of claim 5 wherein the transformation reduces the number of calibrations needed for a laboratory calibration.

9. The method of claim 5 wherein the transformation mathematically combines two of the individual analyte responses.

10. The method of claim 9 wherein the transformation is defined as $$x_1 = [(z_1 - a_{12})^{a11} - a_{13}] \div [(z_2 - a_{22})^{a21} - a_{23}]$$

$$x_2 = [(z_2 - b_{12})^{b11} - b_{13}] \div [(z_1 - b_{22})^{b21} - b_{23}]$$

wherein $z_1$ and $z_2$ are the measured analyte responses;
wherein $x_1$ and $x_2$ are transformed responses;
wherein $a_{11}$, $a_{12}$, $a_{13}$, $a_{21}$, $a_{22}$, and $a_{23}$ are coefficients that can be calibrated.

11. The method of claim 5 wherein the transformation uses one or more coefficients that are not determined on a regular user calibration schedule.

12. The method of claim 5 wherein the transformation uses one or more coefficients that are determined on a user lot schedule.

13. The method of claim 5 wherein the selected measuring process is HPLC.

14. The method of claim 5 wherein the selected measuring process is immunoassay.

15. The method of claim 5 wherein the selected measuring process is one of electrophoresis, capillary electrophoresis, spectrometry, chromatography, surface plasmon resonance.

16. The method of claim 5 wherein one or more of the analytes are proteins, carbohydrates, or nucleic acids.

17. The method of claim 5 wherein the analytes are glycoproteins.

18. The method of claim 17 wherein one of the analytes is hemoglobin A1c.

19. The method of claim 5 wherein the two or more are a glycosylated form of hemoglobin and total hemoglobin.

20. An apparatus for measuring a ratio of concentrations of two or more analytes, said apparatus comprising:
a measuring module capable of measuring responses of the two or more analytes in a sample;
a memory to store the measured analyte responses from the measuring module;
a computer readable medium containing computer readable code having instructions for executing one or more conversion methods that defines the ratio of the concentrations of the two or more analytes as a direct function of the measured responses of the analytes obtained from the measuring module, wherein the direct function includes a multi-variable regression model that outputs the ratio of the concentrations, and wherein the multiple variables of the regression model include the two or more analyte responses; and
a processor to execute the computer readable code on the computer readable medium in order to calculate the ratio of the concentrations of two or more analytes using the one or more conversion methods.

21. The apparatus of claim 20 wherein the measuring module uses a multi-plex immunoassay to measure the analytes responses.

22. A non-transitory computer-readable medium containing computer readable code having instructions for determining a ratio of concentrations of different analytes in a sample, the code comprising:
code for measuring responses of two or more analytes in a sample using a selected measuring process to obtain two or more individual analyte responses of the two or more analytes;
code for selecting a conversion method that defines the ratio of the concentrations of the two or more analytes as a direct function of the two or more individual responses of the analytes obtained from the selected measuring process, wherein the direct function includes a multi-variable regression model that outputs the ratio of the concentrations, and wherein the multiple variables of the regression model include the two or more analyte responses; and
code for computing the ratio of the concentrations of the two or more the analytes of the sample using the selected conversion method and using the measured analyte responses from the sample.

* * * * *